United States Patent
Wikfors et al.

(10) Patent No.: US 9,163,618 B2
(45) Date of Patent: Oct. 20, 2015

(54) AUTOMATED CONVERSION BETWEEN SFC AND HPLC

(75) Inventors: Edwin E. Wikfors, Landenberg, PA (US); Kimber D. Fogelman, Hockessin, DE (US); Terry A. Berger, Englewood, FL (US)

(73) Assignee: Agilent Technologies, Inc., Santa Clara, CA (US)

( * ) Notice: Subject to any disclaimer, the term of this patent is extended or adjusted under 35 U.S.C. 154(b) by 408 days.

(21) Appl. No.: 13/530,931

(22) Filed: Jun. 22, 2012

(65) Prior Publication Data

US 2013/0048095 A1 Feb. 28, 2013

Related U.S. Application Data

(63) Continuation-in-part of application No. 12/230,875, filed on Sep. 5, 2008, now Pat. No. 8,215,922.

(60) Provisional application No. 61/075,251, filed on Jun. 24, 2008.

(51) Int. Cl.
*G01N 1/00* (2006.01)
*F04B 11/00* (2006.01)
*F04B 23/06* (2006.01)
(Continued)

(52) U.S. Cl.
CPC .............. *F04B 11/0075* (2013.01); *F04B 23/06* (2013.01); *G01N 30/32* (2013.01); *G01N 30/34* (2013.01); *G01N 2030/326* (2013.01); *Y10T 137/0352* (2015.04); *Y10T 137/7722* (2015.04)

(58) Field of Classification Search
CPC ....... G01N 30/34; G01N 30/32; G01N 30/20; G01N 30/02
USPC ......................................................... 73/61.56
See application file for complete search history.

(56) References Cited

U.S. PATENT DOCUMENTS

| 2,943,844 A | 7/1960 | Gustafson |
| 3,374,607 A | 3/1968 | Fisher et al. |

(Continued)

FOREIGN PATENT DOCUMENTS

| DE | 2843920 | 4/1980 |
| EP | 0275933 | 7/1988 |

(Continued)

OTHER PUBLICATIONS

Office Action mailed May 2, 2013 for Chinese Application No. 200980129909.4.

(Continued)

*Primary Examiner* — Hezron E Williams
*Assistant Examiner* — Rodney T Frank

(57) ABSTRACT

An apparatus, system, and process of converting a standard, high performance liquid chromatography (HPLC) flow path to a flow path suitable for supercritical fluid chromatography (SFC) are described. This reversible technique is applied to a variety of flow configurations including binary, high pressure solvent mixing systems and quaternary, low pressure solvent mixing systems than can be conventionally operated or automated. The technique is generally applied to the fields of supercritical fluid chromatography and high pressure liquid chromatography, but users skilled in the art will find utility for any flow system where pressurization components must be periodically applied to and removed from both ends of a flow stream in an automated manner.

20 Claims, 29 Drawing Sheets

(51) Int. Cl.
*G01N 30/32* (2006.01)
*G01N 30/34* (2006.01)

(56) References Cited

U.S. PATENT DOCUMENTS

| | | | |
|---|---|---|---|
| 4,042,326 A | 8/1977 | Kallos | |
| 4,095,472 A | 6/1978 | Mowery, Jr. | |
| 4,373,864 A | 2/1983 | Massey et al. | |
| 4,429,584 A * | 2/1984 | Beyer et al. | 73/864.21 |
| 4,478,720 A | 10/1984 | Perrut | |
| 4,599,049 A | 7/1986 | Gordon et al. | |
| 4,624,625 A | 11/1986 | Schrenker | |
| 4,690,689 A | 9/1987 | Malcosky et al. | |
| 4,753,581 A * | 6/1988 | Hiscock | 417/539 |
| 4,781,824 A * | 11/1988 | Allington | 210/101 |
| 4,814,089 A | 3/1989 | Kumar | |
| 4,845,985 A | 7/1989 | Berger | |
| 4,850,806 A | 7/1989 | Morgan et al. | |
| 4,880,543 A | 11/1989 | Khosah et al. | |
| 4,883,409 A | 11/1989 | Strohmeier et al. | |
| 4,892,654 A | 1/1990 | Nickerson | |
| 4,962,662 A | 10/1990 | Berger | |
| 4,990,076 A | 2/1991 | Lynch et al. | |
| 5,009,778 A | 4/1991 | Nickerson et al. | |
| 5,065,789 A | 11/1991 | Eslinger | |
| 5,087,360 A | 2/1992 | Wright et al. | |
| 5,089,124 A | 2/1992 | Mahar et al. | |
| 5,094,741 A | 3/1992 | Frank et al. | |
| 5,108,264 A | 4/1992 | Abdel-Rahman | |
| 5,139,681 A | 8/1992 | Cortes et al. | |
| 5,151,178 A | 9/1992 | Nickerson et al. | |
| 5,151,250 A | 9/1992 | Conrad | |
| 5,178,767 A | 1/1993 | Nickerson et al. | |
| 5,198,115 A | 3/1993 | Stalling et al. | |
| 5,234,599 A | 8/1993 | Cortes et al. | |
| 5,240,603 A | 8/1993 | Frank et al. | |
| 5,281,406 A | 1/1994 | Stalling et al. | |
| 5,305,232 A | 4/1994 | Chimowitz et al. | |
| 5,322,627 A | 6/1994 | Berger et al. | |
| 5,340,476 A | 8/1994 | Berger et al. | |
| 5,344,311 A | 9/1994 | Black | |
| 5,346,622 A | 9/1994 | Klee et al. | |
| 5,360,320 A | 11/1994 | Jameson et al. | |
| 5,378,229 A | 1/1995 | Layer et al. | |
| 5,403,089 A | 4/1995 | Kuo et al. | |
| 5,431,545 A | 7/1995 | Knight et al. | |
| 5,458,783 A | 10/1995 | Levy et al. | |
| 5,462,431 A | 10/1995 | Ahmady | |
| 5,584,989 A | 12/1996 | Jameson | |
| 5,601,707 A | 2/1997 | Clay et al. | |
| 5,614,089 A | 3/1997 | Allington et al. | |
| 5,620,663 A | 4/1997 | Aysta et al. | |
| 5,630,706 A | 5/1997 | Yang | |
| 5,653,876 A | 8/1997 | Funke | |
| 5,653,884 A | 8/1997 | Smart et al. | |
| 5,716,525 A | 2/1998 | Nickerson | |
| 5,738,498 A | 4/1998 | Allington et al. | |
| 5,755,559 A | 5/1998 | Allington et al. | |
| 5,797,719 A | 8/1998 | James et al. | |
| 5,843,311 A | 12/1998 | Richter et al. | |
| 5,888,050 A | 3/1999 | Fitzgerald et al. | |
| 5,996,818 A | 12/1999 | Boje et al. | |
| 6,071,408 A | 6/2000 | Allington et al. | |
| 6,162,022 A | 12/2000 | Anderson et al. | |
| 6,183,635 B1 | 2/2001 | Klee et al. | |
| 6,241,890 B1 * | 6/2001 | Clay et al. | 210/634 |
| 6,260,407 B1 | 7/2001 | Petro et al. | |
| 6,294,088 B1 | 9/2001 | Allington et al. | |
| 6,309,541 B1 | 10/2001 | Maiefski et al. | |
| 6,319,410 B1 | 11/2001 | Allington et al. | |
| 6,345,528 B2 | 2/2002 | Petro et al. | |
| 6,413,428 B1 * | 7/2002 | Berger et al. | 210/634 |
| 6,450,146 B1 | 9/2002 | Dickerson et al. | |
| 6,503,396 B2 | 1/2003 | Kim et al. | |
| 6,561,767 B2 | 5/2003 | Berger et al. | |
| 6,648,609 B2 | 11/2003 | Berger et al. | |
| 6,652,240 B2 | 11/2003 | Wichert | |
| 6,652,753 B2 * | 11/2003 | Berger et al. | 210/634 |
| 6,656,354 B2 * | 12/2003 | Berger et al. | 210/198.2 |
| 6,755,074 B2 | 6/2004 | Davison et al. | |
| 6,923,916 B1 | 8/2005 | Hiraku et al. | |
| 6,979,362 B2 | 12/2005 | Jackson | |
| 6,997,685 B2 | 2/2006 | Lemmen | |
| 7,048,517 B2 | 5/2006 | Berger et al. | |
| 7,144,502 B2 | 12/2006 | Fermier et al. | |
| 7,257,987 B2 * | 8/2007 | O'Brien et al. | 73/23.41 |
| 7,621,171 B2 * | 11/2009 | O'Brien | 73/23.41 |
| 2002/0014106 A1 | 2/2002 | Srinivasan et al. | |
| 2003/0026704 A1 | 2/2003 | Berger et al. | |
| 2003/0054561 A1 | 3/2003 | Gelernt | |
| 2004/0018099 A1 | 1/2004 | Berger et al. | |
| 2006/0219618 A1 | 10/2006 | Witt et al. | |
| 2008/0101970 A1 | 5/2008 | Witt et al. | |

FOREIGN PATENT DOCUMENTS

| | | |
|---|---|---|
| GB | 2475300 | 5/2011 |
| WO | WO2013062635 | 5/2013 |

OTHER PUBLICATIONS

Berger, "Separation of Polarsolutes by Packed Column Supercritical Fluid Chromatography", Journal of Chromatography A, vol. 785, pp. 3-33, 1997.

Extended European Search Report mailed Sep. 12, 2013 for Application No. EP13168579.4.

Office Action mailed Apr. 25, 2014 for Chinese Application No. 200980129909.4.

* cited by examiner

AUTOMATED CONVERSION BETWEEN SFC AND HPLC

STATEMENT OF PRIORITY

This application is a continuation-in-part of U.S. application Ser. No. 12/230,875 filed on Sep. 5, 2008 for "A COMPRESSIBLE FLUID PUMPING SYSTEM FOR DYNAMICALLY COMPENSATING COMPRESSIBLE FLUIDS OVER LARGE PRESSURE RANGES."

FIELD OF THE INVENTION

The present invention relates to methods and systems for pumping compressible fluids. More specifically, it relates to pumping compressible fluids in high pressure applications.

BACKGROUND

Industrial pumping takes many forms, all with the general requirement of transporting fluids or slurries through a process stream. Pumps are selected based on the application requirements including head pressure, metering accuracy, temperature, particle tolerance, fluid viscosity, cost, safety, service rate and a variety of other parameters. Pumps can generally be classified in two categories. Positive displacement pumps isolate discrete volumes of the working fluid and force them to move in a controlled direction. Kinetic pumps operate by adding kinetic energy to the system which creates a local increase in fluid velocity. Kinetic energy is converted to potential energy, i.e. pressure, at the pump output.

FIGS. 1-3 show a variety of different positive displacement pumps. In FIG. 1, a lobe pump is illustrated. This pump type is designed for low pressure, high volume applications where high particle loading may be an issue. The rotating lobes 2, 2' of the pump head 1 are intentionally designed with loose tolerances to prevent physical contact and wear. The loose mechanical tolerance allows pressurized fluid to leak back to the low pressure side. This limits the pressure head the pump can reach generally to less than 20 bar. FIG. 2 illustrates a second type of rotary pump called an external gear pump. The pumping operation is similar to the lobe pump, but tolerances of the gear pump may be made arbitrarily close. As a result, gear pumps can obtain pressures heads of several hundred bar and pump fluids of viscosities from 0.05 to 100000 cP. Significant wear of the gears 3, 3', especially at high pressure and temperature results in variable leakage back to the low pressure side. Both styles of rotary pumps can be isolated in sealed enclosures 4 and driven by magnetically coupled pump motors. This has the tremendous advantage of preventing external leaks of fluid without the use of dynamic seals. Magnetic coupling has lower torque limits than direct drive, however, so gear pumps are generally available only to less than 30 to 50 bar differential pressure. A final valuable characteristic to lobe and gear pumps is that they are considered both continuous and pulseless.

Reciprocating pumps, such as the one shown in FIG. 3, remain a primary industrial means of pumping fluids when high purity, high pressure [e.g. >100 bar to more than 1000 bar] and high precision [e.g. <1% flow variation] are needed. Reciprocating pumps come in several formats including mechanical and pneumatic piston pumps, and mechanical and hydraulic diaphragm pumps. Such pumps are characterized by having one or more heads 5 which transfer fluid between a low pressure input and a higher pressure output. Each pump head contains a means of physically adjusting the internal volume available to the pumped fluid. In operation, each pump head 5 uses a piston 7 driven by a cam 8 that alternately aspirates fluid from the input 6 by increasing the available pump head volume, then dispenses the fluid to the output 7 by decreasing this volume. Most reciprocating pumps are designed to flow in only one direction. Flow direction is controlled by a series of check valves 6', 7' that isolate the pump head from the output pressure during aspiration and from the input pressure during dispensing. The output pressure is generally controlled, not by the pump, but rather by the downstream resistance-to-flow of the process flow stream serviced by the pump.

Reciprocating pumps are characterized by the number of pump heads they utilize. A pump with a single pump head is referred to as a simplex pump. Duplex, Triplex and Quad pumps refer to pumps with two, three and four heads respectively. Two or more pumps heads are required to provide pseudo-continuous flow since one pump head can be delivering while the other is aspirating. However, since the very nature of the movement involves stopping and restarting in opposing motions, reciprocating pumps can only emulate continuous rotary pumps approximately. In general, the greater number of pump heads for a given flow rate, the lower the pulsation of the output stream.

When fluid being pumped by a piston pump is relatively incompressible, these pumps are frequently referred to as metering pumps, since the volumetric flow of the fluid is presumed to match the mechanical volumetric displacement of the piston or diaphragm in the pump head. An excellent example of a metering application of a reciprocating pump is a low pressure syringe pump, in which a glass syringe draws in an aqueous solution and dispenses it very accurately to a downstream reservoir. Under this low pressure use [generally less than 2 bar] the volumetric compression of aqueous solutions is almost immeasurable and thus the presumption of accurate displacement is correct.

When reciprocating pumps are used with very compressible fluids such as permanent gasses, they are frequently called compressors or gas boosters. Gas boosters represent an ideal example of the influence of fluid compressibility on pump performance. In this case, the typical application is to increase the pressure of the gas between the input and output. A fundamental characteristic of gas boosters is the compression ratio. The compression ratio is simply the ratio of the maximum fluid volume a pump head can isolate between its check valves at the peak of its intake stroke to the minimum volume it can reduce to at the end of its delivery stroke. Hence, a compression ration of 7:1 indicates the total volume at intake is seven times greater than the residual fluid volume at the end of delivery.

FIG. 4 displays the compression or delivery stroke of a pump head in a gas booster. In this figure, the pump head 10 is comprised of cylinder 12, piston 14, and input and output check valves 16 and 18 respectively. During the delivery stroke, the cylinder internal volume has three distinct regions: compression volume 20, delivery volume 22 and residual volume 24. During compression, volume is systematically decreased and thermodynamic work is performed on the fluid and it tends to heat up. Higher temperature and lower volume cause an increase in the fluid pressure. The effect of the temperature increase is that the fluid reaches the delivery pressure earlier in the pump stroke than calculated by a simple isothermal volumetric displacement. If no heat were lost to the piston or cylinder walls the heating would be called adiabatic heating, which can be readily calculated from entropy tables for a given gas. Heat generated in the fluid is generally a source of inefficiency since it delivers the gas at a considerably lower density than desired. A cooling step is frequently required in the boosting process to remove the waste heat of compression so that downstream vessels can be filled more densely with the pressurized gas.

It is nearly impossible for a robust pump head design to leave no residual fluid at the end of the delivery stroke. Too close machining tolerances can cause a greater rate of wear and early failure of sealing surfaces. FIG. 4 shows the residual volume of gas remaining at the end of the piston stroke. In general, for gas pressure boosting applications it is very desirable to make this volume as small as possible and to make the compression ratio large. Hot residual gas in the pump head causes a further decrease in pumping efficiency, since it must first expand to below the input pressure before new fluid can enter the pump head during aspiration. Finally, compressive heating of the pump head itself will warm the entering gas to a lower density and reduce the amount of fluid entering with each aspiration.

An examination of the output flow of a gas booster reveals the ultimate difficulty in pumping compressible fluids. For each pump head, the aspirate stroke is expected only to fill the pump head volume and not deliver fluid to the output. The dispense stroke, on the other hand, is expected to deliver fluid to the output. In a piston based gas booster, as the piston moves forward to expel the fluid, temperature and pressure rise, but no fluid is released until the output pressure is reached. If the input pressure is 1 bar and the output pressure is 2 bar, almost half the piston stroke is used just to compress the fluid before delivery begins. As output pressure rises, a smaller and smaller volume of the delivery stroke is released to the output stream. By the time an output pressure of 7 bar is achieved in a booster with a 7:1 compression ratio almost the entire stroke is used for compression with little or no volume released to the output stream.

If aspiration and dispense strokes are of equal duration, fluid is delivered only 25% of the complete pump cycle in the 2 bar case. Even in a duplex booster pump, flow would only occur 50% of the time. By the time 7 bar output pressure was achieved, the pump would be delivering <1% of the time. As a result, most booster pump applications are pressure based and not flow based. These are not considered metering pumps at all since the work for compression makes it impossible to reliably calculate the volume of delivery per stroke.

Some applications require pumps that can meter fluids continuously and accurately at high pressure. For all fluids, including gasses, liquefied gasses, liquids and supercritical fluids, pressurization results in corresponding decrease in volume and increase in temperature to some degree. In general the compression effect is orders of magnitude different between permanent gasses such as Helium, liquefied gasses such as liquid carbon dioxide [$LCO_2$] and true liquids such as water. At high enough output pressures, however, even water must be measurably compressed before being delivered to an output flow of a pump flow stream.

Water essentially behaves like a spring with a definable force constant that indicates how much volume change will occur per applied unit of pressure. This force constant is referred to as compressibility and is often reported in units of inverse bar [$bar^{-1}$]. The generally accepted compressibility value for water at 20 C is $46 \times 10^{-6}$ $bar^{-1}$. Hence at 1 bar additional pressure, a volume of water would reduce 0.0046%; at 10 bar 0.046%; at 100 bar 0.46% and at 1000 bar 4.6%. In fact, water does not behave as a perfect spring and the compressibility value tends to become smaller at very high pressure so the 4.6% volume change is somewhat overstated, Nevertheless it is clear that between 100 and 1000 bar a measurable portion of the dispensing pump stroke will be dedicated to compression of the water and thus cause an interruption to the continuous flow of a standard duplex pump. Water is considered one of the more incompressible liquids. Table 1 lists compressibility values for other representative organic solvents at 20° C. Generally these organic solvents range from two to three times more compressible than water.

TABLE 1

Compressibility values for various pure liquids at 20 C.

| Liquid | Compressibility ($\times 10^{-6}$ $bar^{-1}$) |
|---|---|
| Water | 46 |
| Tetrahydrofuran | 93 |
| Acetonitrile | 99 |
| Benzene | 94-95 |
| Chloroform | 97-101 |
| Methylene chloride | 97 |
| Carbon tetrachloride | 103-105 |
| Ethanol | 110-112 |
| Methanol | 121-123 |
| Acetone | 123-127 |
| n-Heptane | 140-145 |
| n-Hexane | 150-165 |
| Diethyl ether | 184-187 |

In practical terms then, for a reciprocating pump, compressibility is the fraction of the piston stroke required to increase the fluid pressure to delivery pressure. Compressibility compensation refers to reducing the period of deficit flow and/or adding extra flow to the flow path to compensate for this deficit. Also for the purpose of clarity, a compressible fluid shall be defined in terms of the fluids density variation in going through the metering pump and the corresponding need for compensation. It is common for high pressure metering pumps to have specified volumetric flow accuracy relative to the operational or maximum flow value. Without further calibration, pumps must rely on the assumption that mechanical displacement is equivalent to fluidic delivery. Hence a pump specified to 1% accuracy could not compress the aspirated fluid by more than 1% during the piston delivery stroke. Compressible fluids would be those that exceed this amount of compression [and corresponding change in density] during a delivery stroke. As a result, compressibility compensation is required to bring the pump to the operating specification.

Whether a fluid is compressible by this definition is tied to the delivery pressure of the fluid. A single fluid aspirated from an atmospheric reservoir, may be below this compressible fluid threshold at low delivery pressures but above it at high delivery pressures. For example, for a pump with a 1% accuracy specification, water [compressibility=$46 \times 10^{-6}$ $bar^-$] does not become compressible until it reaches approximately 225 bar, while hexane [compressibility=$150 \times 10^{-6}$ $bar^{-1}$] becomes compressible at approximately 65 bar. When a fluid's compressibility exceeds the pump specification at some operational level, some action must be taken to adjust the pump's performance. This corrective action is generally referred to as compressibility compensation.

Values of the compressibility for a given liquid are dependent on both temperature and pressure. Generally as pressure increases the compressibility value goes down while at higher temperatures the value increases. Other factors such as dissolved gasses in the liquid can affect the compressibility value. Mixing two or more liquids can have unpredictable effects on the solutions compressibility. Table 2 shows the very nonlinear behavior of mixtures of water and methanol at 20 C.

TABLE 2

Compressibility Values for Water:Methanol Mixtures

| Water-methanol, (v-v) | Compressibility (×10⁻⁶ bar⁻¹) |
|---|---|
| 100-0 | 46 |
| 80-20 | 40 |
| 60-40 | 46 |
| 50-50 | 52 |
| 40-60 | 56 |
| 20-80 | 86 |
| 10-90 | 117 |
| 0-100 | 121 |

Many laboratory and industrial applications require continuous high pressure flow of fluids similar to those listed in Tables 1 and 2. One example is high pressure mixing of fluids, where periodic lapses of flow from one process stream will cause significant local concentration variability. Such variability can lead to improper dosage levels of active pharmaceutical ingredients or imbalance in the ratio of reactants in chemical flow reactors. At the laboratory scale, a prime example of the need for continuous high pressure flow is the case of high pressure metering pumps used in high performance liquid chromatography [HPLC]. Modern HPLC systems are commonly comprised of two separate pump modules to allow the high pressure, controlled mixing of two solvents at a time to create a well mixed mobile phase for chromatographic elution.

FIG. 5 shows the basic components for an HPLC pump of prior art. HPLC pump 30 is an example of an electric cam driven pump. In this case motor 32 rotates shaft 34 to rotate eccentric cams 36 and 38 to provide a reciprocating motion of pistons 40 and 42 contained in pump heads 44 and 46 respectively. As each piston aspirates, fluid is drawn from fluid reservoir 56 through input check valve 48 or 50 respectively. Output check valve 52 or 54 remains sealed during aspiration. During the delivery stroke, input check valve 48 or 50 is shut while output check valve 52 or 54 opens to deliver fluid to process stream 58. The cam drive shown in FIG. 5 is just one example of an HPLC pump. Others would include ball screw drives, pneumatic drives and hydraulic drives coupled to the pistons 40 and 44. Much of the remaining discussion focuses on pumping a fluid using compression compensation of laboratory-type HPLC type pumps that are similar in design to pump 30.

Requirements for pumps used in typical laboratory HPLC instruments are very demanding. Pumps must be able to deliver at very high pressures [up to 400 bar for traditional HPLC and as high as 1000 bar for recent ultrahigh performance LC systems]. A 2000 bar ultrahigh performance LC system is expected. HPLC pumps must also be able to handle fluids of ultra-high purity without contributing detectable contamination. In addition, for a given flow rate, the volumetric delivery of fluid is expected to remain constant within narrow limits [<1% variation] across the majority of the operational pressure range. Finally, the same pump is also expected to vary flow precisely over at least an order of magnitude of range in periods as short as one minute. This is the result of the need for a technique called gradient elution in which the two solvents controlled by separate pumps are systematically adjusted in relative composition from a weakly to a strongly eluting mixture while maintaining a constant combined flow rate.

An interesting effect of the mixing of two different solvents is that the viscosity of the combined mixture may vary widely over the course of the gradient run. As viscosity increases the resistance to flow of the chromatographic system causes a pressure rise. Thus even as one solvent is decreasing in its flow rate during the gradient elution, the pressure the pump experiences can be rising. FIG. 6 displays the viscosity behavior of various compositions of two binary mixtures: water: methanol 62 and $CO_2$:methanol 64. Mole fraction of methanol is graphed on the x-axis and viscosity in millipascal-seconds is graphed on the y-axis 68. For typical HPLC applications, the water: methanol plot 62 clearly demonstrates extreme nonlinearity that can occur over the range of compositions. Each pump must be able to adjust to both varying output pressure and flow during gradient runs. Further, most long term applications require that the pumps must repeat this performance within a specification limit over their useful lifetime in order to provide truly valid data for the HPLC system.

In order to meet such demanding performance specifications, Modern HPLC pumps must address the issue of compressibility. Compounding the problem of compressibility is the fact that a majority of standard HPLC pumps have compression ratios less than 3:1. This means that there exists a minimum residual volume of 50% of the full stroke volume of each piston that never leaves the pump head's internal volume. This residual volume must be compressed and expanded on each stroke which adds a burden of at least 50% to the compressibility compensation effort. This sets a significantly lower limit for a given fluid on the maximum pressure at which it may be effectively pumped.

To counter the periodic flow lapses resulting from fluid compressibility, pump manufacturers have devised a number of techniques to suppress their negative effects. Pulse dampeners are routinely used in high pressure equipment to attenuate the pressure fluctuations associated with periodic discontinuities in flow. Pulse dampening attenuates pressure noise from the system, but does not always correct flow issues. Consider the case of pumping a moderately compressible liquid at high pressure. The piston is set to deliver at a fixed rate of displacement to achieve the desired flow. Since the compression part of the stroke delivers no flow without makeup or compensating flow, followed by the delivery portion which delivers at the correct flow rate, only negative flow pressure pulsations are seen at the pump output. No amount of pulse dampening will smooth the flow to the desired flow rate. It will always be less than required. A common technique to counter this issue is simply to increase the mechanical rate of the piston so that the average flow matches the expected flow. However, as seen earlier, the amount of compression needed per stroke varies with output pressure. As a result, very specific knowledge of the fluid characteristics would be needed to make this correction at all flows and pressures.

Simple correction to improve average flow also neglects yet another problem, local variations in the flow compositions. It is a frequent practice to place a single pulse dampener in binary pumps [a single pump module which contains two separate duplex pumps] at a location downstream of the mixing point of the two fluids. Thus each flow lapse of one pump due to compression results in a segment of flow that is dramatically enriched in the other fluid. This local enrichment, especially of high strength elution solvents can cause serious perturbations of the separation in HPLC. Further, since composition changes usually are accompanied by detectable changes in the refractive index of the fluid, significant noise can be experienced at any optical detectors in the flow system. This noise typically limits the ability of the system to detect very small quantities of material in the flow stream.

To limit the effect of compression, HPLC pump manufacturers have also attempted to shorten or eliminate the compression time. This has been done by accelerating the piston displacement during compression to minimize the period of flow lapse. Again, while a fixed acceleration period is useful over a limited range of pressures, in order to compensate over the entire pump range the acceleration period must be proportional to the output pressure. This feature has been accomplished in some modern HPLC pumps which can allow entry of CCF values up to $150 \times 10^{-6}$ $bar^{-1}$.

In the last several years, much focus has been placed on new ultrahigh performance chromatographic systems extending beyond the 400 bar pressure limit. This change has dramatically increased the awareness of compressibility as a major factor in pump performance. Traditional pumps have been redesigned to improve compression ratios. Special calibration algorithms have been adapted to determine empirically the compressibility of fluids over the entire range of pump operation to account for the actual nonlinearity of compression correction factors.

One area that has not been well addressed in the pursuit of higher pressures is the thermodynamic work that must be performed on the pumped fluids. As ultimate pressures reach 1000 or even 2000 bar, even well behaved fluids such as listed in Table 1 experience significant compression. Just as in the gas booster example above, significant compression, especially at the accelerated rate required for compression compensation, can result in significant heating of the fluid. Heating in turn leads to variability in fluid density and compressibility. Further, heat generated in the fluid during compression can communicate to pump head walls and warm incoming fluid further affecting density. Over the course of variable gradient flow, such factors are continuously varying and make it quite difficult to determine precise composition of the mixed components of the binary mobile phase.

Compressibility levels encountered in ultrahigh performance chromatographic systems are very similar to those encountered in supercritical fluid chromatography (SFC) over the last twenty years. SFC is a subset of traditional HPLC that uses liquefied $CO_2$ as one of the components of the mobile phase. As a liquefied gas, $CO_2$ must be delivered at high pressure to the pump head in order to remain in the liquid state. This is normally accomplished by connecting a tank containing both liquid and vapor $CO_2$ in thermal equilibrium. A dip tube in communication with the $CO_2$ liquid of the tank is plumbed directly to the pump head. Generally, chilling of the pump head and pre-chilling of the fluid are necessary to insure that $CO_2$ remains in the liquid state during pump aspiration. Special grades of high purity $CO_2$ are used in SFC to prevent dissolved components of less pure $CO_2$ from affecting the optical clarity of the mobile phase. Mixtures of $CO_2$ and common organic solvents also tend to have higher changes in refractive index than corresponding water: organic solvent mixtures so that small rapid variations in composition are more observable with optical detectors.

As mentioned, pumping of liquid $CO_2$ takes special precautions to insure a continuous liquid supply into the pump head. The compressibility of liquid $CO_2$ is also a major factor since it is typically as much as ten fold higher than most of the organic liquids mentioned in Table 1. Further, compression of $CO_2$ between 60 bar [approximate tank pressure] and 400 bar [the maximum system pressure] can raise the fluid temperature more than 25 C. Such a temperature rise dramatically alters the density of the delivered fluid and introduces even more requirements for pump control.

The vast majority of commercial SFC pumps are modified HPLC pump designs. One manufacture uses the equation of state of $CO_2$ to calculate fluid compressibility at various pumping pressures. A second manufacturer uses mass flow sensors to determine the average mass flow of the system and adjusts the pump speed to maintain a controlled average mass flow. Another reported technique is to use a specialized duplex pump where each piston is controlled by an independent motor. Pressure sensors allow the filling pump head to pre-compress the fluid to 90% of the output pressure as part of the filling sequence. Triplex pumps are reported that allegedly further reduce flow pulsation. Special algorithms have been created to surge pumps slightly beyond full compression to add a small excess of $CO_2$ flow immediately adjacent to the $CO_2$ deficient region and then allowed the segments to mix by longitudinal diffusion. For all the efforts to date, SFC analysis is still considered to be of lower sensitivity and poorer quantitation limits than standard HPLC. A significant reason for this is higher baseline noise directly related to the methods employed to fully compensate for compressibility.

In most reciprocating pumps an extra flow is added at the end of the compression stroke to compensate for the lack of flow during compression. Without this compensating flow, the pump will deliver inaccurate flow and compositions which become unintended functions of the delivery pressure. Thus, there is a period of no flow, followed by a period of excess flow. The two are intended to cancel each other out. While such compensation assures accurate flow and composition, it increases short term flow and pressure noise, which increases detector noise and degrades detection limits. The much higher compressibility of $CO_2$ compared to normal liquids used in HPLC results in a much longer lapse and larger compensating flow, accounts for most of the degradation in detector noise previously observed in SFC.

Despite the poorer limits of detection, SFC enjoys high popularity in the areas of both preparative separation and analysis. SFC is the technique of choice in the rapidly growing area of chiral separation. This technique is also shown to be two to five times faster than traditional HPLC in separating both chiral and achiral mixtures. In fact, SFC competes favorably with the most advanced state-of-the-art implementations of ultrahigh performance chromatographic systems without the need for extreme pressures, special separation columns and vendor specific consumable hardware. As a result, a high interest remains for this technique if it can be brought closer to the low levels of quantitation available to HPLC.

The general steps of pumping with a piston pump involve aspiration of working fluid into the pump chamber, compressing the fluid to the pump output pressure and delivering the compressed fluid to the output flow stream. In the course of this process thermodynamic work is performed on the working fluid which results in temperature and density changes of the fluid. In addition, the amount of work and corresponding physical change done to the fluid is dependent on both total pressure rise required within the pump head and the physical characteristics of the fluid itself. This variability leads to the poorly metered pumping of fluids of unknown density and requires use of correction factors that are generally inadequate to provide pulse free flow from the pump head. As a result, both systematic and local variations in composition can easily arise in the mixed flow stream of binary and ternary pump systems.

While this discussion has focused a great deal on the needs of low-noise, precise, continuous high pressure pumping in chromatography, the need is truly general. Thus, there is a need for a solution for metering a compressible fluid without the variations that degrade overall quality of the process stream and frequently require addition of further components to correct this quality at the expense of speed, cost or energy efficiency in the process stream.

Liquid chromatography (LC) is a known separation technique for isolating and identifying individual dissolved components contained typically in a liquid sample. The technique uses a liquid mobile phase flowing past an adsorbent stationary phase to achieve separation. The terms high pressure-, medium performance-, high performance-, ultra performance- and ultra-high performance liquid chromatography are generally accepted terms related to the pressure ranges and speed of separation achieved by different LC instrumentation. For the purposes of this application, the term high performance liquid chromatography (HPLC) will be used generically to include all forms of liquid chromatography using positive displacement pumps to propel fluids which are liquids at typical laboratory temperatures and pressures, regardless of the maximum pressure ranges these pumps typically achieve. In other words, abbreviations such as MPLC, UPLC, UHPLC and HPLC common in the art of LC will all be considered under the generic term HPLC. Forms of liquid chromatography not falling under this term would be those where the flow of the liquid mobile phase is driven by gravity, capillary action, pneumatic pressures, centrifugal forces and other means than positive displacement pumps, or where the pumped fluid is not liquid at laboratory conditions of temperature and pressure.

The most common form of HPLC is reversed phase HPLC or rHPLC which uses mobile phases consisting of water and organic solvents to elute mixtures of compounds through a nonpolar stationary phase, such a C18 with the least polar compounds eluting last. These more highly retained compounds in rHPLC can be eluted faster by reducing the polarity of the mobile phase. A less common form of high performance chromatography is supercritical fluid chromatography (SFC), which operates in the same typical pressure ranges as HPLC but instead uses pressurized carbon dioxide at liquid-like densities combined with organic solvents to perform normal phase separations. As the names suggest, normal and reversed phase separations have opposing mechanisms where normal phase uses polar stationary phases and increasing polarity of mobile phase to encourage elution of later eluting polar compounds. Packed column SFC (pSFC) using typical normal phase and chiral phase HPLC columns is the most accepted form of SFC in use today. Because of the different mechanisms, the rHPLC and pSFC techniques are complementary and when applied to the same mixture of compounds, a very different elution order and separation speed and efficiency can result.

Modern HPLC and SFC systems are modular with functions of pumping, sample injection, column thermal control and detection being organized in separate electronic modules collectively controlled and coordinated by a computer workstation. SFC systems typically adds control features including augmented control of the carbon dioxide pumping subsystem and backpressure regulation to the system in order to condition the CO2 flows and pressure to maintain a reproducible monophasic mobile phase in the separation flow path extending at least from the point of sample injection through detection. Both types of chromatography systems can typically be run in either isocratic or gradient elution modes. Isocratic elution mode occurs when the composition of the mobile phase is kept constant during the course of a separation. Gradient elution mode occurs when the composition is varied either continuously or by stepwise changes during the separation. Generally HPLC separations have a constant total flow rate, but some methods also vary flow during the separation. The total flow rates in HPLC are typically much lower than in SFC due the relatively higher viscosities and lower diffusion rates in HPLC mobile phases.

In the course of experimental synthesis of new compounds, as in the pharmaceutical industry, it is beneficial to periodically analyze reaction products either intermediately or at the end of synthesis process to determine the success of the synthesis or at other times during drug discovery and development. Such analyses are performed by chemists that are often not specialists in the use of chromatographic equipment and prefer significant automation in using the systems. In addition, the high cost of certain equipment such as mass spectrometers makes sharing of equipment a common practice in these industries. Since both HPLC and SFC are routinely used in these industries, it would be beneficial to allow users to easily and/or automatically convert between HPLC and SFC in a single instrument configuration. Several attempts to merge the capabilities of the two techniques have been reported, but in all cases, due to the customization typically associated with SFC related pumps, entirely different sets of pumps have been used.

SUMMARY OF THE INVENTION

Embodiments for an automated, reversible means of converting a standard, high performance liquid chromatography (HPLC) flow path to a flow path suitable for supercritical fluid chromatography (SFC) are described. The invention uses a device or process to selectively switch flowpaths to achieve different modes of operation such as HPLC and SFC. Preferably, a single valve, for example a high pressure rotary valve, is used to 1) assure all fluid lines are switched simultaneously, 2) share HPLC modules in both HPLC and SFC modes, 3) maintain a desired fluidic communication between the CO2 pumping subsystem and the system back pressure regulator and 4) provide an adequate means of rinsing the shared fluidic path of incompatible solvents prior to switching between flow paths. The invention is applied to a variety of flow configurations including binary, high pressure solvent mixing systems and quaternary, low pressure solvent mixing systems. The technique is generally applied to the fields of supercritical fluid chromatography and high pressure liquid chromatography, but users skilled in the art will find utility for any flow system where pressurization components must be periodically applied to and removed from both ends of a flow stream in an automated manner.

The various preferred and alterative embodiments of the present invention employ a high pressure rotary valve to achieve changes in the flow configuration to convert a system between HPLC operation and SFC operation. Conversions are performed with the following restrictions. The manufacturer's requirement for products that can be used in a commercial embodiment of an SFC booster pumping system products require that the CO2 booster and BPR be maintained in fluid communication at all times during operation of the system. The requirement is implemented to provide a safe, vented overpressurization path from the CO2 booster via the BPR and as a means of retaining the system in a charged and ready state while operating in alternate chromatographic modes. The created flow systems should as closely as possible represent the flow systems of the unmodified HPLC flow systems and the prior art or newly described SFC flow systems respectively as illustrated in FIGS. 1 through 5. The flow system conversion should result from a single switching of a single rotary valve. Use of multiple valves for conversion makes fluidic system more complex an increase the risk of safety hazards if one valve switches and another fails to switch.

Various described embodiments further improve the art of SFC by combining programmable low pressure formulation of the organic modifier composition with high pressure mixing between the modifier and CO2. This provides the ability of on-demand selection of the strong solvent formulation within the mobile phase previously absent from commercial SFC systems. Such embodiments also realize certain limitations described herein as part of the novel use of quaternary pumps in SFC.

FIGURES

DETAILED DESCRIPTION

Figure 7:
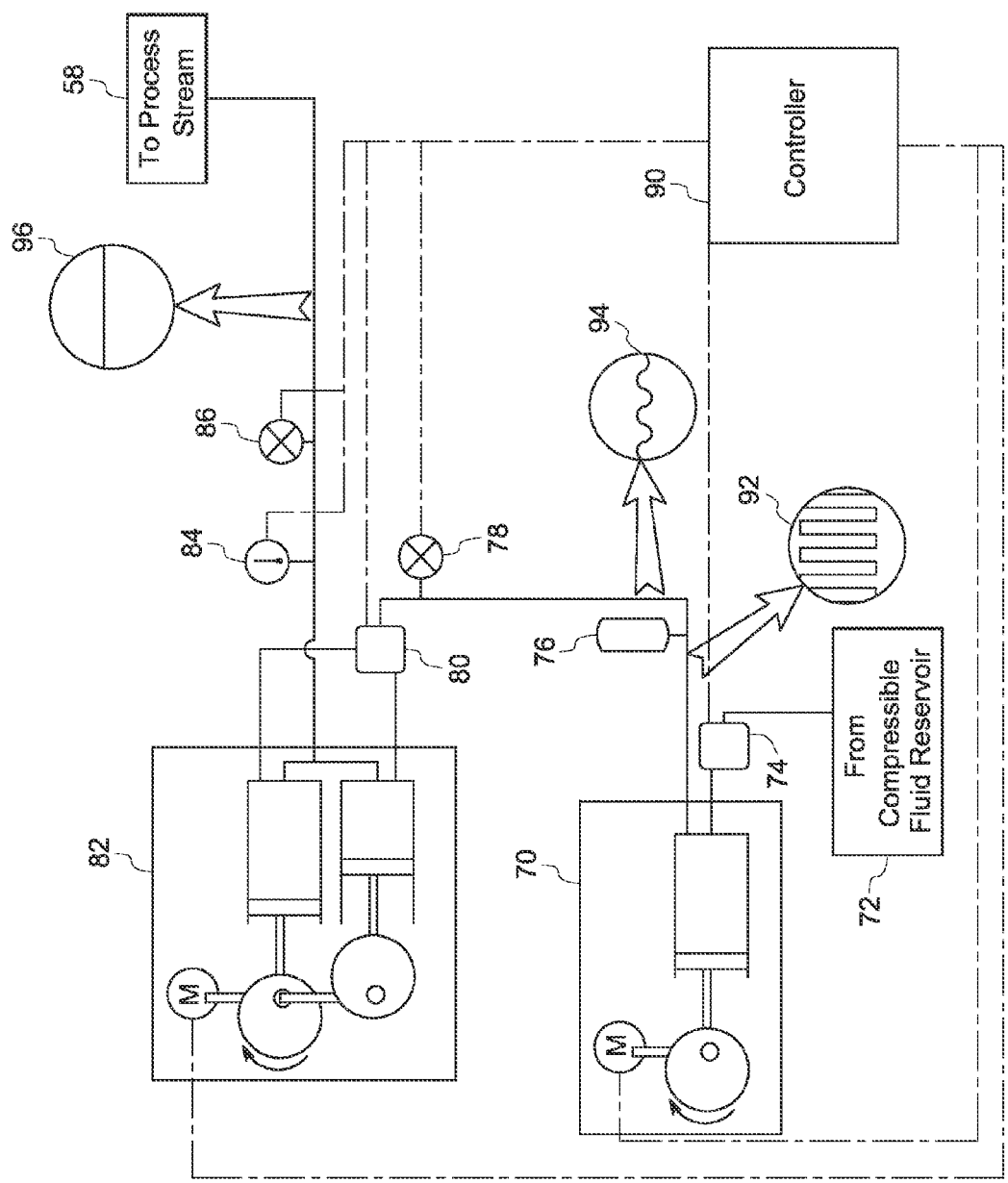
FIG. 7 illustrates the preferred embodiment of a booster pump and metering pump arranged in series for a compressible fluid supply.

Referring to FIG. 7, a schematic illustration of a preferred embodiment of the invention is displayed. Booster pump 70 receives compressible fluid from reservoir 72. An optional prechiller 74 cools the compressible fluid input stream as well as the pump heads of booster pump 70. Booster pump 70 delivers flow to an output flow path containing optional pulse dampener 76, booster pressure sensor 78, and thermal conditioning device 80. Metering pump 82 receives the output flow of booster pump 70 and delivers flow via optional temperature sensor 84 and process pressure sensor 86 to process flow stream 88. Controller 90 receives sensor signals from pressure sensors 78 and 86 and optional temperature sensor 84. Controller 90 further controls optional thermal zones of devices 74 and 80 and controls the pumping speed of booster pump 70. Optionally controller 90 also controls the metering rate of metering pump 82, although this is not a requirement of all applications of the embodiment.

The embodiment of FIG. 7 is comprised primarily of booster pump 70 with booster pressure sensor 78; thermal conditioning device 80; metering pump 82 with process pressure sensor 86 and controller 90. The two pumps 70 and 82 are connected in series. In its simplest operation, once the embodiment is brought to its initial working state, controller 90 periodically reads process pressure sensor 86 and adjusts the speed of booster pump 70 to maintain a pressure at booster sensor 78 within a determined range in the near vicinity of pressure sensor 86. The specific pressure difference between sensors 78 and 86 is application dependent as described in later sections, but the intent is to deliver fluid that is no longer compressible to metering pump 82 as previously defined herein. A preferred range is 0 to 10 bar. Alternatively, a preferred range is within 10% of the output pressure of the second pump. In all cases this difference is within 20% of the output pressure. Thermal conditioning device 80 limits the variation of fluid temperature due to fluidic compression in the booster pump 70. Finally metering pump 82 receives the thermally conditioned fluid at a pressure very near to the delivery pressure and accurately meters the fluid to the process stream without the need of further compression. The beneficial result of the preferred embodiment is that virtually all fluidic compression is performed by booster pump 70 with excess heat of compression removed by thermal conditioning device 80 while metering pump 82 provides accurate and precise volumetric delivery of the working fluid into the process stream with very low pulsation.

An obvious requirement of booster pump 70 is that it should be capable of delivering fluid at least in slight excess of the maximum application requirements. It is preferred that the pump be able to deliver significant excess of volumetric flow to account for any system leaks or changes in density that may occur between the two pumps after compression. Similarly, booster pump 70 must be able to achieve pressures within the full scope of the process requirement. Further, the response of the pump must be rapid enough to allow the booster to maintain pressure within a narrow range of the specified pressure delta between sensors 78 and 86 even when the process stream backpressure is varying at a rapid rate.

Booster pump 70 does not need to be a particularly low pulsation pump. FIG. 7 displays as an example a simplex booster pump with equivalent aspirate and dispense strokes. As a result, delivery only occurs with a maximum 50% duty cycle. When high compressibility fluids such as liquid $CO_2$ are pumped, the delivery portion of the stroke is further reduced due to incomplete compressibility compensation. As a result, relatively large pressure fluctuations can be observed in the flow path between the pumps which can make it more difficult to regulate the desired boost pressure. The volume in the flow path itself can provide some buffering. A simple way to further reduce the pulsation is the introduction of optional pulse dampener 76 between the two pumps. Pressure traces 92 and 94 demonstrate the reduction of pulsation that can be easily achieved by pulse dampener 76. In our laboratory, use of a simplex pump to provide the booster pump function in the preferred embodiment resulted in greater than 12 bar pressure fluctuations at operating pressure near 150 bar as represented by trace 92. Addition of a simple pulse dampener consisting of a high pressure vessel with an internal volume of approximately 25 mL reduced the pulsation to less than 2 bar as shown in trace 94. In this case the compressible fluid itself acted as its own dampening agent.

A second optional component to the booster pump 70 in the preferred embodiment is prechiller 74. Cooling power may be supplied by heat exchange with a chilled circulating fluid, by thermoelectric components such as peltier chillers, or by direct Joule-Thompson expansion of refrigerants in the vicinity of the entering fluid transfer lines. Prechiller 74 may have several purposes. The primary purpose is to insure the efficient operation of the booster pump. By lowering temperature of the working fluid, especially in the case of liquefied gasses, cavitation, or sudden evaporation, of the working fluid during aspiration can be prevented. Prechiller 74 may also be directly affixed to the pump heads of booster pump 70 to remove a significant amount of the transferred heat of compression that may build up within the pump head.

An additional, high value use of prechiller 74 is as a condensing unit to liquefy compressible fluids supplied to the booster in vapor form. Such capability creates a much broader variety of sources of the working fluid. A premier example is liquefying $CO_2$ from a lower purity source such as a beverage grade $CO_2$ reservoir. By sampling from the gas phase of the tank rather than the liquid phase, the $CO_2$ is actually distilled, which removes nonvolatile impurities from the working fluid. Purity of the $CO_2$ working fluid can be elevated well above the purity of traditional high purity $CO_2$ grades such as SFC or SFE grades costing at least an order of magnitude more. By sampling from a high pressure cylinder, the $CO_2$ pressure is already very near the room temperature gas-liquid equilibrium pressure. As a result, only the heat of vaporization needs to be removed [a few watts of cooling per gram] to form liquid $CO_2$. From this point, lowering the temperature further, e.g. below 10 C, gives sufficient margin to prevent cavitation of the liquid $CO_2$ during the aspiration portion of the piston stroke.

Another advantage of delivering vapor $CO_2$ to the pump is the dramatically reduced cost of distributing a modest pressure gas stream throughout a laboratory or process site as opposed to delivering high pressure liquefied gas. If the prechiller is capable of cooling $CO_2$ below −20 C the pressures of $CO_2$ available to most dewar cylinders and bulk tank installations become available as sources. Hence a high power prechiller can truly lower the operating cost of the $CO_2$ supply as well as allow its safe transport though low pressure piping within a facility. The economics are largely driven by the relative cost of bulk beverage grade $CO_2$ at less than $0.10 per pound compared to SFC grade $CO_2$ at more than $7.00 per pound—a 70-fold increase.

Booster pressure sensor 78 and process pressure sensor 86 are typically strain type gauges placed in fluidic communication with the flow stream by use of a tee. Sensors with accuracy error at or below 0.25% of full scale are easily obtained and typically sufficient. If one of the sensors is of higher accuracy, the other may be easily calibrated to reference it. Full scale range should be selected as close as possible to the application's required maximum pressure for best accuracy. Generally precision of 0.1% and burst pressure greater than 3-4 times the highest required process pressure are also desirable performance specifications.

Thermal conditioning device 80 has the task of regulating the temperature of the fluid between booster pump 70 and metering pump 82. Most frequently, this regulation involves transferring excess heat of compression generated in the booster pump out of the fluid prior to entry into the metering pump. In most applications, thermal conditioning device 80 will attempt to bring the working fluid temperature to an isothermal state near the ambient temperature of metering pump 82. Further, the device may be actively or passively controlled. Minimally, the thermal conditioning device is a simple transfer line between pumps 70 and 82 that transfers heat to or from the ambient air by radiation or convection.

Use of an active thermal conditioning device can extend the performance of the preferred embodiment to several modes of operation discussed in detail later. First, active heat transfer can stabilize the fluid temperature in conditions where the ambient temperature is not well controlled. Second, it can transfer heat at a much larger scale than passive devices. For applications that require high variation in flow or pressure change that result in large heat-of-compression variations, an active conditioning device can respond much more rapidly that a passive device. As a result the maximum rate of change of the process stream can be significantly faster. In addition, some applications require the working fluid to be held at a temperature away from ambient. In these cases the thermal conditioning device may be required to either heat or cool the fluid as well as interface directly the pump heads of metering pump 82.

Figure 1:
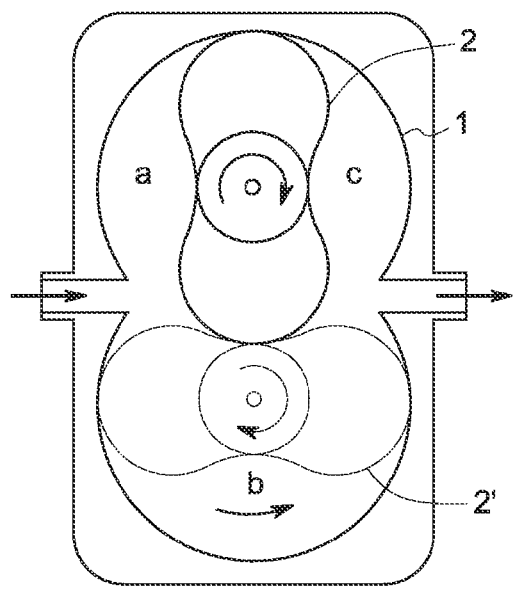
FIG. 1 is a diagram of a rotary lobe pump head.
Figure 2:
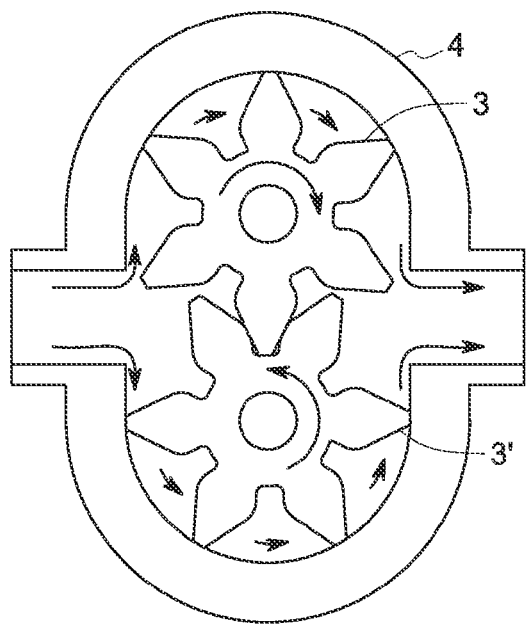
FIG. 2 is a diagram of an external gear pump head.
Figure 3:
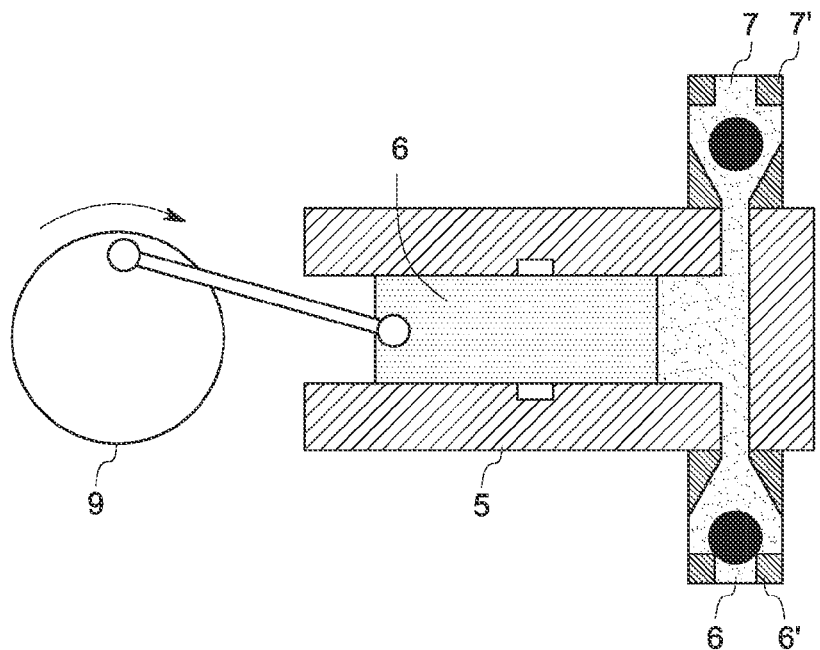
FIG. 3 is a diagram of a piston pump head.
Figure 4:
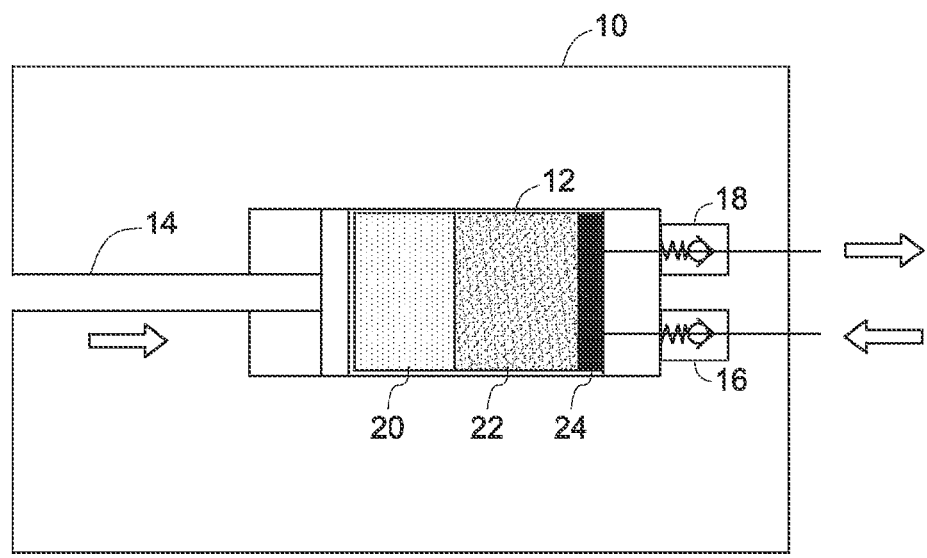
FIG. 4 is a detail of a piston and cylinder arrangement in a pump where the cylinder has filled with a compressible fluid.
Figure 5:
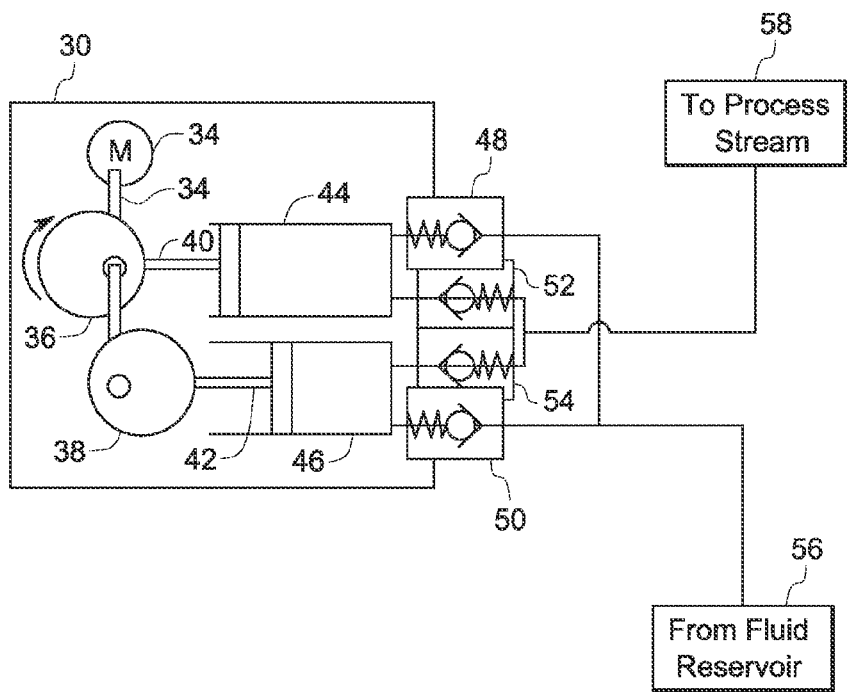
FIG. 5 is a schematic of a high pressure HPLC pump of prior art.

In FIG. 7, metering pump 82 is displayed as a duplex piston pump with both pistons coupled to the same drive system and in fact identical to pump 30 of FIG. 5. The coupling of the two pistons is actually of significant advantage in the preferred embodiment, since the delivery piston receives power both from the electric, pneumatic or hydraulic drive system, and also from the working fluid force applied to the aspirating piston. As a result, the drive system of metering pump 82 must deliver only a small fraction of the torque necessary to raise the working fluid to the high output pressure of the process stream. Further, cavitation of the working fluid under these conditions is extremely unlikely. The requirement does remain that the pump heads of the metering pump must be rated for the high output pressures and that any seals isolating the working fluid from the ambient pressure must be rated for low leakage and, preferably, long maintenance intervals between failure. High purity of the pump head components is another frequent requirement of the design.

Use of a duplex piston pump as metering pump 82 may impose another requirement on the preferred embodiment. In instances when the check valves used in such pumps are passive and unassisted by springs or any other mechanical closure devices, the pressure set point of booster pump 70 must always be controlled slightly below the metering pump output pressure. If the booster pressure exceeds the metering pump output pressure, both input and output check valves will open at the same time and flow will proceed regardless of the metering pump flow rate. As a result, control of the volumetric flow would be lost. In addition, pressure variations generated by the booster pump would be transferred to the process stream.

So long as the input check valve is closed during the delivery stroke of metering pump 82, the metering pump actually serves as a final noise filter in the preferred embodiment. During aspiration of each pump head, the metering pump is in communication with the potentially noisy flow stream provided by the booster pump via the input check valve. However, during delivery the input check valve closes and the working fluid is isolated from this noise. Small density variations of the working fluid caused by the pressure fluctuation during filling can result in a single minor compression variation at the start of the delivery stroke. However, the vast majority of noise is not transferred. This effect is illustrated in FIG. 7, by comparing pressure traces 94 and 96. Periodic pressure ripple exiting pulse dampener 76 results in only minor compression perturbation in the output metering pump 82.

Optional temperature sensor 84 can take many forms. The primary goal of this sensor is to report the fluid temperature accurately to within one degree Centigrade with a response time shorter than the fastest flow or pressure change of the process stream. Suitable sensors may include thermocouples, thermistors, platinum RTD probes, tubing RTD measurements, etc.

Operation Modes of the Preferred Embodiment
Volumetric Flow Delivery Mode

The default mode of flow delivery for the preferred embodiment of FIG. 7 is controlled volumetric delivery. By optimizing the use of metering pump 82 in an isothermal low pressure differential environment, the assumption that fluid delivery is equivalent to mechanical displacement of the delivery piston becomes valid. For a number of process applications, particularly those without dramatic changes in pressure, the pulseless volumetric delivery of compressible fluids meets all requirements in a manner superior to existing technologies.

One advantage to the volumetric delivery mode is that it requires no specific knowledge of the flow demand of metering pump 82 to operate. Pumps 70 and 82 can be controlled by totally different controllers with no communication between them other than the pressure signals. As flow demand increases, the pressure between the pumps decreases and the booster is triggered to increase flow. Similarly, as the process flow stream pressure increases and more compression of the working fluid are needed, the booster increases its rate. Even in the case of decreasing pressure and flow as seen for part of the flow gradient of FIG. 6, the system can remain in control by decreasing the booster pump 70 rate more than necessary to allow the working fluid in pulse dampener 76 to expand and lower its pressure.

The ability to decouple control of the two pumps from the same controller further allows the embodiment to be easily incorporated into existing pumping systems. Careful examination of FIGS. 5 and 7 shows that the HPLC pump 30 is virtually identical to metering pump 82. This directly implies that existing HPLC pumps, for example, can be easily enhanced in performance with the simple addition of the remaining required flow components of FIG. 7 including at least booster pump 70 and booster pressure sensor 78; thermal conditioning device 80; process pressure sensor 86 and controller 90. In this example, HPLC pump 30 is easily converted to being capable of pumping very compressible fluids such as liquid $CO_2$ and as a result, the HPLC system it services can be converted to an SFC. Such conversion is described more fully later regarding alternative embodiments and their applications.

The preferred embodiment as well as alternative embodiments is also tolerant of minor leaks in booster pump 70 or any flow components immediately prior to metering pump 82. Leaks of fluid in the system result in no loss or degradation in volumetric metering performance of the system. Since the booster pump is only required to provide pressure and not quantitative flow, small leaks simply result in a higher rate of pumping speed. Thus, critical pumping applications can continue even as a minor failure point develops. This lends to the robustness of the system in critical applications. It is preferred that the control software provides diagnostic routines that can evaluate the quality of sealing in the system during non-critical periods as a regular maintenance feature.

Mass Flow Delivery Mode

One aspect of volumetric delivery that has not been described in detail is the fact that as process pressure varies, the density of the working fluid may also vary significantly. This is particularly true since the working fluids discussed are considered compressible at the typical delivery pressure range of the process. Hence, a pumping system that delivers a constant isothermal volumetric flow across a wide range of pressures [and therefore densities] is actually varying the physical mass of working fluid delivered to the process stream per unit time.

A solution to the problem exists in the case of the preferred embodiment for some applications. Addition of optional temperature sensor 84 at the output of metering pump 82 gives controller 90 access to both current pressure and temperature of the working fluid as it enters the process stream. These parameters are referred to as state variables and many fluids have been evaluated over a very wide range of temperature and pressure to determine fundamental physical parameters such as density, entropy, enthalpy, viscosity, heat capacity, etc. As a result, knowledge of the particular fluids density can easily be extrapolated from critical density tables of temperature and pressure available in the literature. Further, if the full equation of state is known for a fluid, the density can be directly calculated by insertion of the current values of the state variables. Even in the absence of resources such as critical tables and equations of state, the information can be obtained by direct calibration of the preferred embodiment flowing though a calibrated reference device such as a coriolis mass flow meter.

Regardless of the method of gathering the data, if it can be made available in real time to controller 90 by means, for example, of a programmed lookup table, the controller can control the rate of metering pump 82 to deliver a desired mass flow rather than a volumetric flow. This control mode is quite different from the volumetric flow mode above in two ways. First, it requires specific knowledge of the pumped fluid as a technique of translating easily measurable state variables to fluid density. Second, it requires either that controller 90 control both pumps, or that the separate controller of metering pump 82 be given access to both the temperature and pressure data to allow it to control mass. In either of the later cases special interfacing is required for metering pump 28 which may not be available in cases of existing pump systems. The mass flow control mode continues to share the other benefits of the preferred embodiment including low pulsation and high precision of flow delivery.

Constant Density Delivery Mode

In some cases, mass flow delivery is required, but it is not possible to obtain control of the flow rate of metering pump 82 in real time. Pumps with constant flow rates or predetermined flow profiles are common in industry. In these specific cases it remains possible to control the mass flow rate across a significant range of pressures for fluids of which the critical density tables are available. Mass control is implemented by maintaining a constant density in the working fluid delivered to the metering pump regardless of delivery pressure. In the previous example, knowledge of the state variables of temperature and pressure provided a calculation of density which in turn allowed calculation of a proper flow rate to deliver a specified mass rate.

In this case, adjusting the working fluid temperature with thermal conditioning device 80 to achieve a constant density at the current pressure again provides a direct proportional relationship between the volumetric delivery of the pump and mass flow. Hence at high pressures, where the ambient temperature density of a fluid is likely to be high, increasing the fluid temperature will lower the density to the target value based on the lookup value provided to the controller. Similarly, at low pressures, compressible fluids can become less dense at room temperature. Chilling the fluid below ambient temperature can restore the target density. In this control mode, it may also be necessary to use thermal conditioning device 80 to control the metering pump head temperature to prevent density changes as fluid passes through the pump head.

Constant density delivery should not considered for processes with wildly fluctuating pressures since the time constants for heating and cooling can be significant. However, temperature control in lieu of flow control can be used in many applications were zeroing in on a desired mass flow rate requires minor adjustment over the process pressure range. Such control would not be possible within a single stage pumping system where density variability due to heat of compression cannot be easily compensated.

Constant Compressibility Mode

An additional operation mode of the preferred embodiment is to deliver working fluid of constant compressibility to allow pumps which automatically incorporate compressibility compensation to perform in a pulse free manner. As described earlier, compressibility factors are determined by the change in density per bar of applied pressure. However, at higher pressures, the compressibility factor declines as the fluid becomes more resistant to compression. As a result, a single compressibility factor typically cannot be used for a given fluid over the large pressure ranges associated with some applications.

Figure 8:
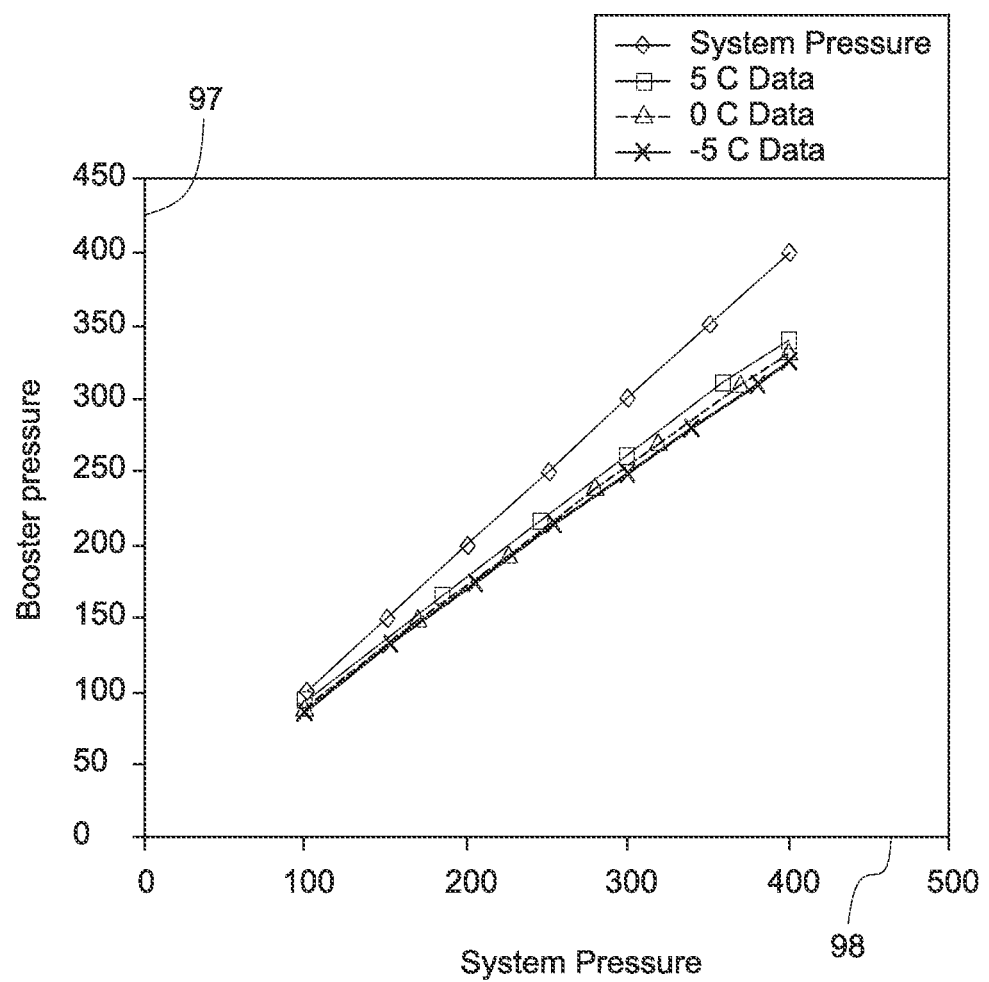
FIG. 8 is a graph of process pressure vs. booster pressure needed to achieve constant compression at different fluid temperatures.

In normal operation, the preferred embodiment attempts to reduce fluid compressibility on the metering pump to a level so low that it is unnoticeable. Some pumps have built-in minimum compressibility compensation either as part of a cam shape or by programming of the piston motion. Knowledge of the density of a fluid at various temperatures and pressures allows one to calculate an appropriate compression factor. For example, if a fixed compression term of 0.5% of the delivery volume is machined into a cam, controller 90 can determine the density of the fluid at the current output temperature and pressure, then use a lookup table to determine the pressure at which the density is 0.5% less and regulate booster pump 70 to provide that pressure at sensor 78. This entire sequence can be performed continuously so that even under constantly changing process conditions, the compressibility remains 0.5% of the full stroke. FIG. 8 shows the relationship between process sensor 86 and booster sensor 78 necessary maintain constant compressibility at various working fluid temperatures.

First Alternative Embodiment

Figure 9:
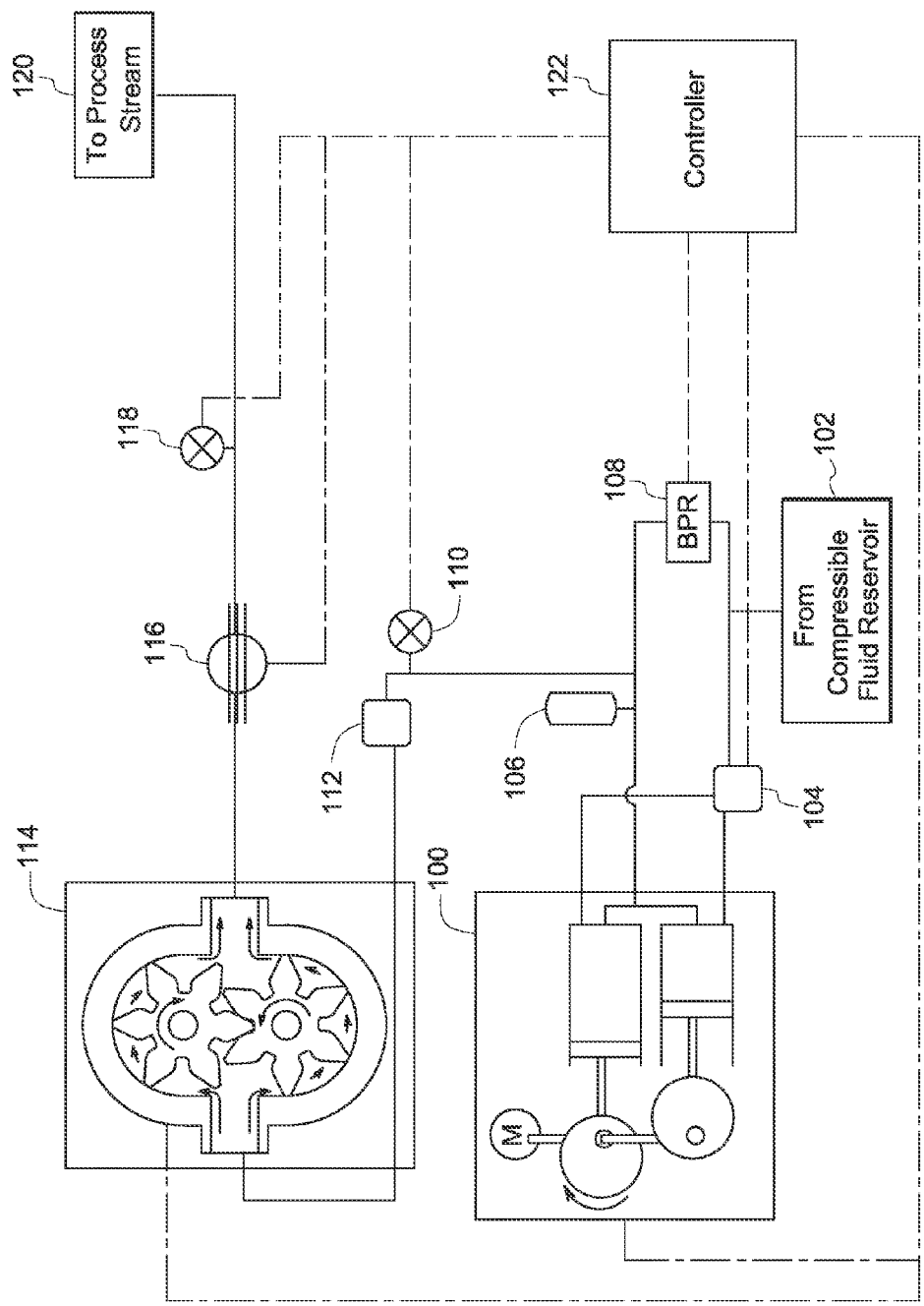
FIG. 9 illustrates an alternative embodiment using a continuous gear pump for the metering stage and a BPR to regulate booster pressure.

An alternative embodiment of the invention is displayed in FIG. 9. Booster pump 100 receives compressible fluid from reservoir 102. The fluid is chilled at prechiller 104 prior to entering the booster pump. On exit from the booster, the fluid passes optional pulse dampener 106 and the flow is then split between back pressure regulator (BPR) 108, which returns a portion of the flow to the low pressure side of the booster, and the flow path leading to metering pump 114. The later flow path also contains booster pressure sensor 110 and thermal conditioning device 112. The output flow stream of metering pump 114 leads to optional flow sensor 116, process pressure sensor 118 and finally to process stream 120. Controller 122 receives the signals of pressure sensors 110 and 118 and flow sensor 116. The controller also controls back pressure regulator 108 and prechiller 104. Optionally, the controller also controls the flow rate of booster pump 100 and/or metering pump 114.

In this embodiment, booster pump 100 is displayed as a duplex rather than simplex pump. Preferably, any pump that can provide both sufficient flow and pressure while maintaining the working fluid purity can be suitable as a booster pump, which is one of the unexpected results of the present invention. Generally noise from the pump can be attenuated sufficiently by a properly sized pulse dampener. The selection of a duplex pump adds to system robustness. In FIG. 7 it was demonstrated that a simplex pump was sufficient for most applications. If the duplex pump is selected to simply provide double the flow of this simplex then each pump head would only have half the work. This should extend seal life in the duplex pump considerably. Further, even in the event of total failure of one pump head of the pump, the second is able to maintain system pressure and flow. In critical applications, users may select to use a duplex pump just for the redundancy it offers.

Use of a duplex booster pump in this embodiment further illustrates that the booster pump described can actually be comprised of a plurality of pumps. In this example the duplex pump acts as two simplex pumps supplying fluid in parallel. Such implementation may be merited when the use of two or more inexpensive pumps can economically replace a more expensive single pump. The pumps may be operated proportionally with each performing a proportion of the flow, or in a backup mode where one pump is engaged only when necessary to makeup flow to affect higher total flow or to accelerate the change of output pressure. In a similar manner, use of booster pumps in series can provide a technique to supply higher delivery pressures than a single pump due to limitations such as the compression ratio of each pump. For the purposes of further discussion, the term booster pump may include one or a plurality of pumps connected in series or parallel arrangements to supply the metering pump with an adequate pressure of fluid.

In some situations is it desirable to maintain booster pump flow at a constant speed that may improve pumping efficiency or eliminate the need of controlling the flow from controller 122. In this situation, booster pump 100 must be set at a pumping rate high enough to deliver maximum process mass flow at the highest pressure of the process stream. Volumetric flow delivery by booster pump 100 may substantially increase at lower pressures where the fluid is less compressed. BPR 108 provides an ability of releasing flow in excess of that needed to maintain pressure for metering pump 114. Minimally, BPR 108 is a simple on/off valve that acts to maintain pressure within a narrow desired pressure range. Preferably, BPR 108 acts as an adjustable bypass valve for returning excess fluid back to the low pressure side of the pump. The BPR is electronically controlled and creates a variable restriction for the return flow. As a result pressure in the flow path to metering pump 114 can be maintained over the entire range of process operation. BPR 108 also provides an ability of rapidly re-equilibrating pressure in applications such as gradient elution chromatography where the system is periodically reset to an initialized state.

Metering pump 114 in this alternative embodiment is shown as an external gear pump. More specifically, it is preferred that the pump head be of the magnetically coupled type which is fully sealed against leaks to the ambient environment. Magnetic coupling typically has a limit of 30-50 bar pressure differential due to the maximum torque the drive can produce without slipping. In the embodiments, much lower pressure differentials are expected. So long as the outer enclosure is designed to withstand maximum process working pressures, the pumping method is available. Because of their sealed nature, hermetic gear pump heads require no maintenance for seals. At low pressure differentials, wear on gears and subsequent back leakage should also be at a minimum. Selection of rotary pump heads such as gear pumps is an alternative when very long maintenance intervals are required. Additionally, the continuous operation of a gear pump can further reduce any pressure pulsation noise generated by the pumping system.

Optional flow sensor 116 is presented as a technique of positive feedback to the alternative embodiment. The flow sensor may be a calibrated thermal sensor or a coriolis type mass sensor. In the case of the using the gear pump 114 as the metering pump, this flow sensor can be mounted on either side of the metering pump, since no leakage outside the flow path can occur.

Differences between this alternative embodiment and the preferred embodiment do not significantly affect the performance of the invention. It can be readily seen by one skilled in the art that the alterations of this alternative embodiment can be taken individually or in the whole to adapt the invention to a particular application Second Alternative Embodiment A second alternative embodiment of the invention illustrated in FIG. 10 demonstrates the extensibility the invention to a plurality of process streams. In this alternative embodiment, a single booster pump 124 supplies pressurized working fluid from compressible supply 152 to multiple metering pumps 126, 128, and 130 connected in series with the booster pump 124 and in parallel with each other. A pre-chiller installed between compressible fluid supply 152 and booster pump 124 to cool any incoming compressed gas to below its supply temperature and chill the booster pump head to prevent cavitation. Other flow devices including pulse dampener 132, booster pressure sensor 134 and thermal conditioning device 136 are positioned in the series line between the booster and all parallel metering pumps. Each metering pump supplies working fluid via a process pressure sensor 138, 140, or 142 respectively, to an individual process stream 144, 146, or 148 respectively. Not shown in FIG. 10 is the controller.

A requirement of this implementation is that process pressures remain within a critical range that allows the booster to maintain a small enough pressure differential for accurate metering of the pump. Flow rates of individual metering pumps may vary and the pressure may also vary so long as the changes occur in all parallel processes. While booster pumps are common in industrial applications to lift the input supply pressure high enough to prevent pump cavitation, it will be appreciated by one skilled in the art that the tracking of input pressure to output pressure as described in this embodiment is a superior means to insure accurate delivery of the metering pumps.

Third Alternative Embodiment

Figure 10:
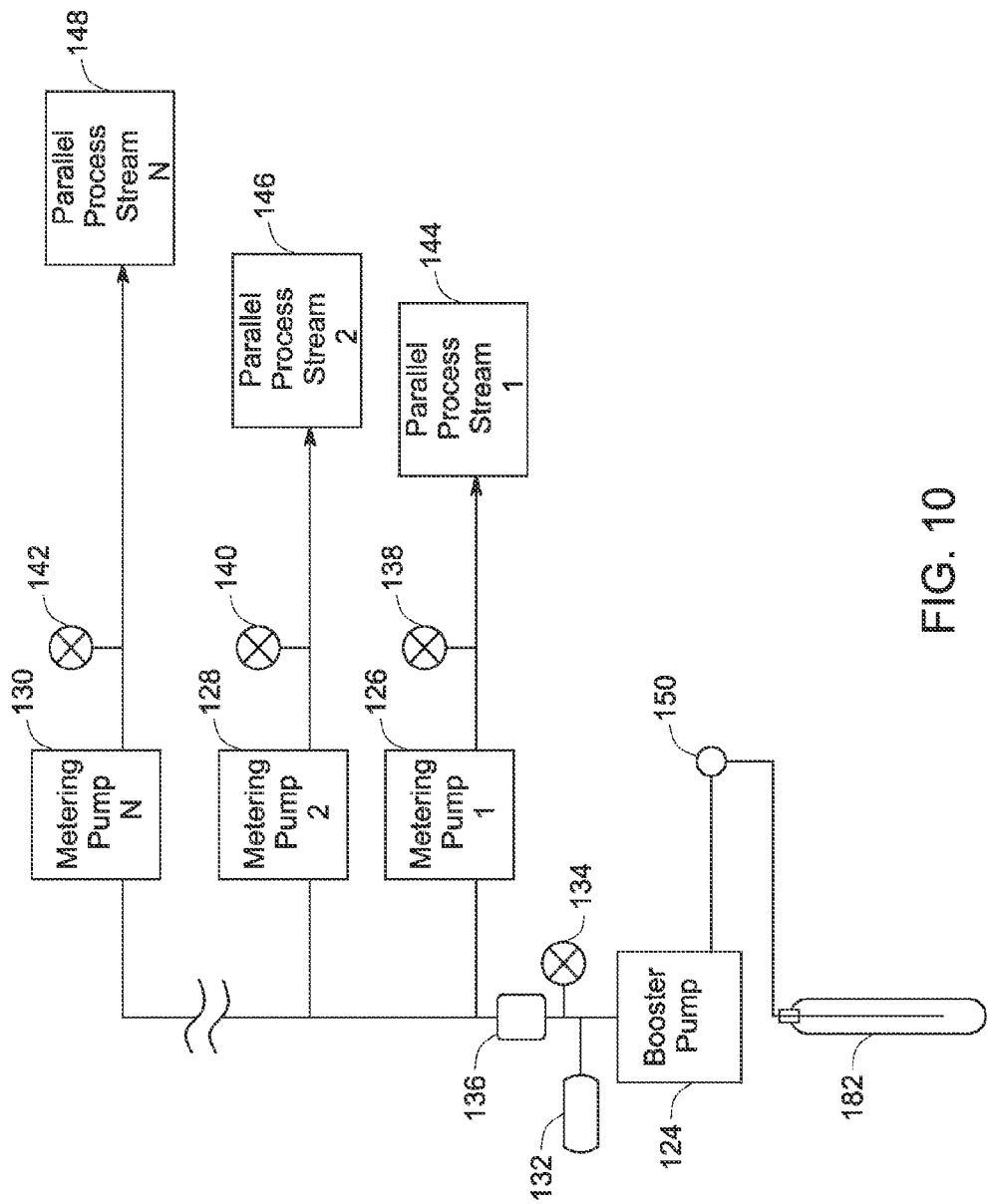
FIG. 10 illustrates an alternative embodiment of a single booster pump for a compressible fluid supply that feeds multiple metering pumps.
Figure 11:
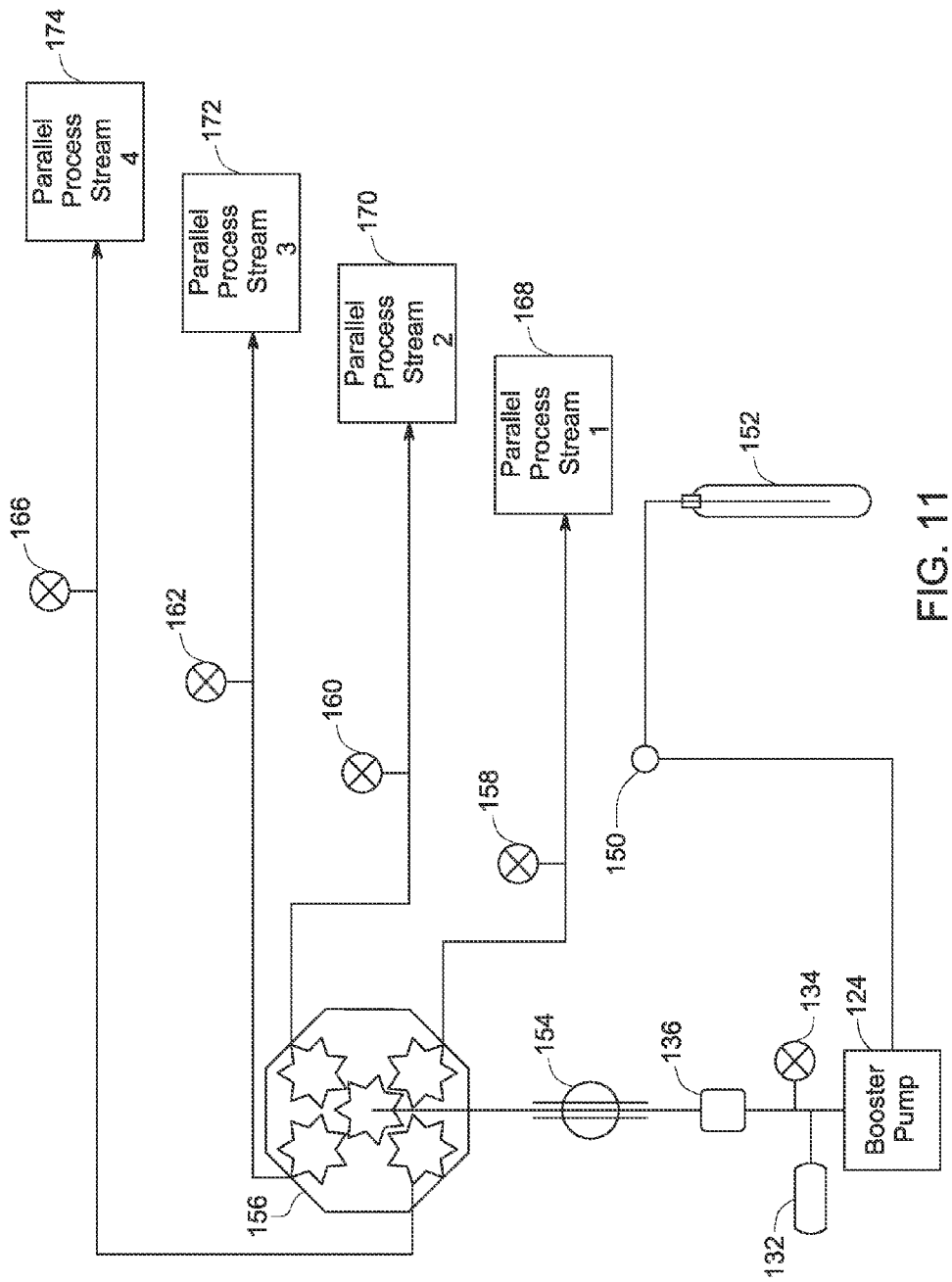
FIG. 11 illustrates an alternative embodiment using a singe boosting stage into a planetary metering pump which produces multiple equivalent outputs servicing separate process streams.

FIG. 11 displays a variation of the parallel processing stream concept from FIG. 10. In this case individual metering pumps 126-130 are replaced with a single drive, multi-output pump device 156. The implementation shown in FIG. 11 as metering pump 156 is a planetary gear pump mechanism which receives a single input and distributes flow evenly between multiple outputs. Alternatively, a pump that can also be considered is the radial piston pump comprised of multiple pairs of opposing pistons in a radial configuration. In this implementation opposing pistons are joined to the same process stream to deliver a pulseless output flow.

Addition of a single flow sensor 154 at the input to the metering pump 156 can indicate total flow that is then distributed evenly between the multiple processes. Pressure sensors 158-166 monitor pressure on each respective multiple outputs of metering pump 156 and provide pressure feedback to a controller of booster pump 124. Each multiple output then feeds into multiple respective process streams 168-174 that are arranged in a parallel configuration.

Applications of the Preferred and Alternative Embodiments
Conversion of HPLC to SFC High performance liquid chromatography (HPLC) systems typically rely on reciprocating metering pumps to deliver accurate and precise volumetric flows with low pulsations. Such performance is needed to achieve reproducible retention times of various compounds uniformly from all similar instruments and to prevent anomalous noise on modern electronic detector signals during chromatographic separations. Multiple pumps are often used to create different compositions of mobile phases such as in gradient elution HPLC methods.

In chromatography, "retention" is a fundamental relationship between a compound and a chromatographic system. In HPLC, retention is a measure of the relative affinity of dissolved components in a sample mixture for the liquid mobile phase vs. the solid stationary phase within a separation column. Compounds that more strongly interact with the stationary phase emerge from the column later than compounds with weaker interactions. Relative retention can be a partial basis for identification of each compound. If the actual flow rate, or composition, of the mobile phase varies in an uncontrolled manner, the fundamental nature of retention and identity is lost. The ability to reproduce the retention behavior from instrument to instrument and laboratory to laboratory is an essential part of the validation and scientific acceptance of HPLC methods.

A fundamental figure of merit for each chromatographic system is the detection limit (the smallest amount that can be detected using a specific detector) for each compound. The lower the detection limit the more widely useful the technique. Excessive flow noise translates to a noisy detector signal which can obscure genuine signals representing the emergence of a small amount of a compound from the stationary phase into the detector. The data system may not even detect a real signal from a small amount of eluting compound. Excessive flow noise degrades detection limits.

Further, lower detection limits generally indicate larger dynamic range of detection, another desirable characteristic that allows both very large and very small signals from different compounds to be displayed, without distortion, in the same chromatographic run. Excess noise decreases dynamic range of the detector (the concentration range over which the detector gives a linear or calibrate-able signal. Slightly less bothersome, the noise can distort measured retention times, causing increased uncertainty in identification. Minimizing flow noise, and subsequent detector noise, has been a long term goal of chromatographic pump development As stated earlier, high performance liquid chromatography imposes a very large set of requirements on the pumping system with regard to pressure and flow variations. With the advent of supercritical fluid chromatography and more recently ultrahigh performance chromatographic systems, existing HPLC designs have required substantial redesign to deal the substantial increase in fluid compressibility as well as higher torque needed at higher pressures. As a result, existing HPLC pumping systems are becoming obsolete as more modern systems take their place. To date, attempts to solve the issues of compressibility have largely centered around mechanical acceleration of the pumping systems to shorten the compressibility effect. Little work has been done to account for metering variations from heat generated within piston due to the thermodynamic heat of compression.

Specialized pumps have been developed both for SFC, to pump highly compressible liquid $CO_2$ at standard HPLC pressures, and for ultrahigh performance LC to deal with the greater range of compressibility of standard HPLC solvents at substantially higher pressures. In the case of SFC pumps, specialization has included adding a prechiller to cool the incoming $CO_2$ to prevent cavitation as well as providing very specific firmware to dramatically extend the ability of the pump to compress the $CO_2$ for delivery. SFC systems further require controllable back pressure regulation to maintain the $CO_2$ in liquid form as it passed optical detectors common in HPLC. The back pressure regulation must remain constant even during variations in flow and composition of the mobile phase.

Mixtures of $CO_2$ and organic modifiers tend to be much better behaved with regard to changes in viscosity than HPLC compositions. Referring back to FIG. 6, one can easily note the linear relationship between viscosity and organic mole fraction for $CO_2$ mixtures. This is in stark contrast to the HPLC curve which varies dramatically well outside the levels of either pure reagent.

Figure 6:
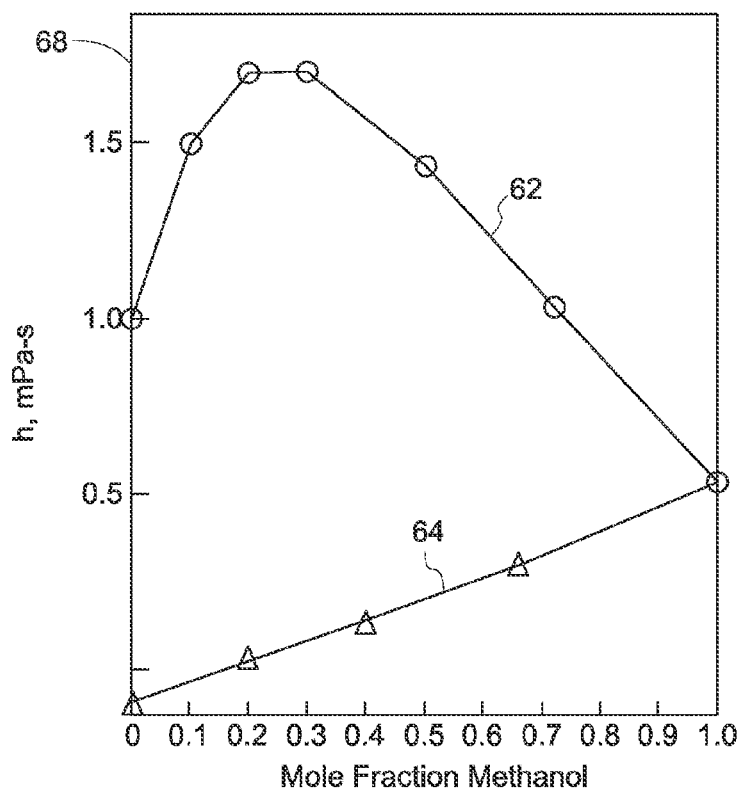
FIG. 6 is a graph of mole fraction modifier vs. dynamic viscosity for two exemplary mobile phase fluids.

FIG. 6 further points out that $CO_2$ mixtures are remarkably lower in viscosity than corresponding HPLC compositions. Viscosity is a measure of the ability of molecules to move past one another in the liquid phase. Lower viscosity reduces the pressure drop across separation columns that are packed with particles in the 1-10 micron size range. Finally, lower viscosity leads to a higher rate of diffusion which accelerates the rate of equilibration between dissolved sample components and the stationary phase. As a result separations simply occur faster in SFC. Gradient elution can be performed in shorter periods. Mobile phase is pumped at higher flow rates. All of these factors compound the need for very high performance pumps used in SFC.

Compressibility of $CO_2$ ranges between 4 and 20 times higher than solvents common to HPLC. This range is well outside the compensation range of most standard HPLC pumps. Hence, in addition to prechilling the input fluid and pump head, $CO_2$ pump 124 must be significantly specialized in its pumping algorithm. Compressibility is nothing more than the fraction of volume change required to raise the pressure one unit such as 1 Bar. Compressibility can be empirically determined, and tables of compressibility can be generated. Compressibility can be calculated using an equation of state if the initial and final pressures and temperatures of the fluid are known. Many HPLC pumps allow the user to input compressibility values for the percent displacement needed to rapidly raise the fluid to the delivery pressure. Compression is adiabatic process, so the actual temperature of the fluid after compression can be much higher than the chiller control temperature, requiring less compression than an isothermal compression. In advanced pumps, the control system automatically searches for the optimum empirical compressibility which delivers accurate flow and suppresses flow noise.

Various ultrahigh performance chromatographic systems face many of the pumping compressibility issues of SFC. Proprietary implementations of these systems not only require specialized pumps, but also specialized column hardware and injectors. Smaller particles are generally used to take advantage of the significantly higher operating pressures and provide separations in a shorter time period. Pumps for these systems are also generally limited to lower flow ranges than traditional HPLC pumps and, so far, the technique has not proved scalable to larger flow systems such as preparative chromatography. A major factor limiting scalability is the extremely high torque required for motors to deliver fluids at such high pressures. Such motors generally reach maximum torque only at a narrow range of speeds and thus are limited in application.

Figure 12:
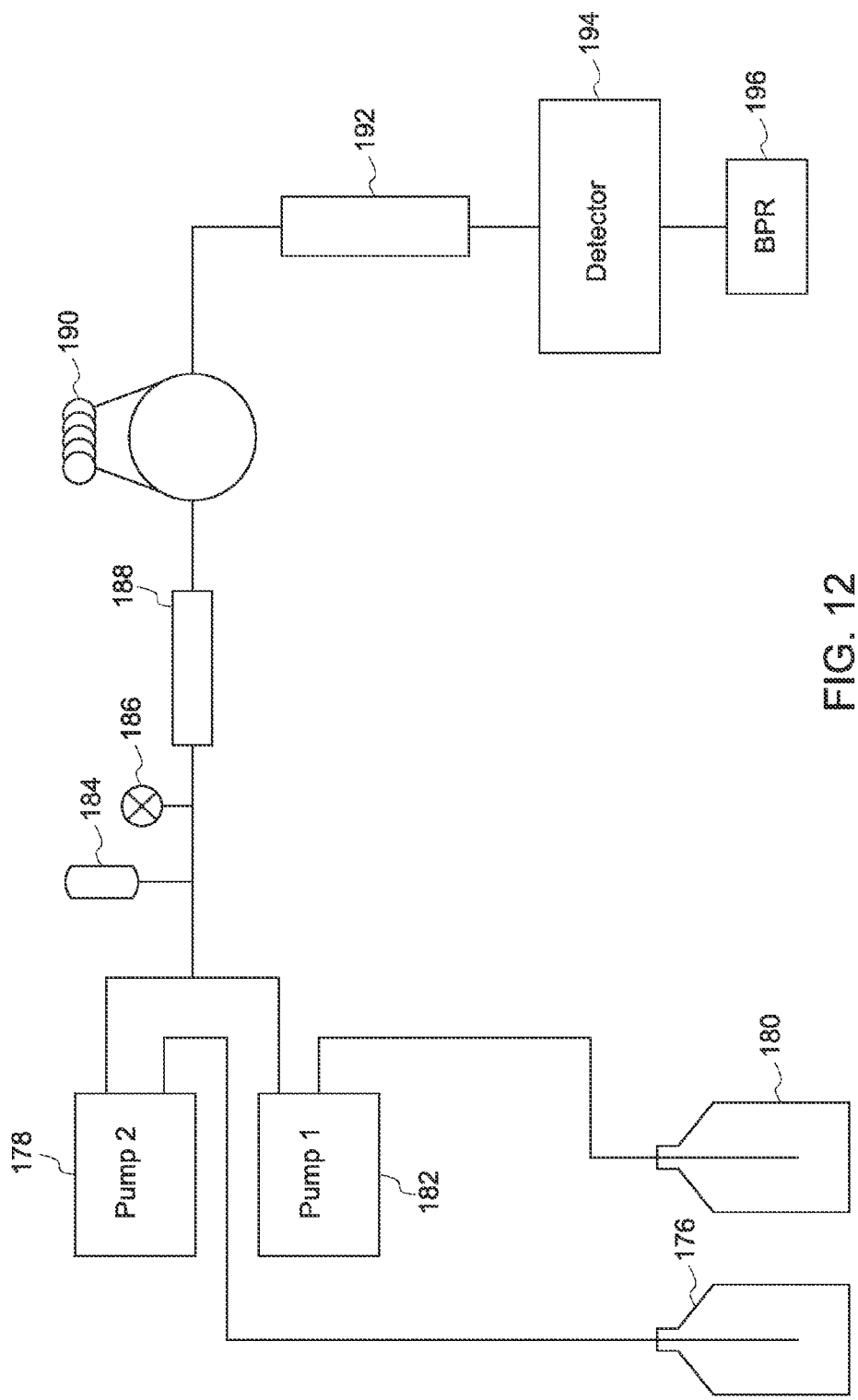
FIG. 12 illustrates is a high pressure liquid chromatography system of the prior art.

FIG. 12 displays a schematic of a modern binary HPLC system of prior art. The system is comprised of a duplex pump 182 which receives a liquid supply [typically high purity water] from reservoir 180. A second duplex pump 178 typically receives an organic solvent of higher compressibility from reservoir 176. The two liquid flow streams mix at a tee then continue past pulse dampener 184 and output pressure sensor 186 through diffusion tube 188, injector 190, separation column 192, detector 194, and BPR 196, before being exhausted to waste or to another process such as fraction collection in preparative systems. Not shown in the FIG. 12 is the system controller that directs the specific operation of the system.

In operation, each pump of the HPLC system of FIG. 12 is set to an initial flow rate to produce a specific composition of mobile phase. The mobile phase is allowed to equilibrate with the separation column. Detectors are adjusted to recognize the signal produced at this initial state as a "baseline" value. To begin an actual separation, the sample loop of injector valve 190 is filled with liquid containing a mixture of dissolved components. The valve is actuated to allow mobile phase to push the sample segment onto the separation column. Individual components of the sample mixture experience different retention times on the separation column and emerge at different times. The detector senses the components and generates an electronic signal different from the baseline value which can later be interpreted for component type and/or amount by the system controller. Back pressure regulator 196 provides sufficient backpressure to prevent disturbances in the detector from outgassing of mobile phase elements.

If the initial mobile phase composition is sufficient to separate all components of the sample in a timely manner, it is maintained over the separation period. This is referred to as isocratic separation. Frequently, the adsorption of some components of a sample is so strong that the initial flow composition would take inordinately long to elute the mixture. A technique called gradient elution is used in these cases. Gradient elution allows the sample application and initial separation of poorly retained components to occur at the initial condition, then ramps the solvent composition to higher concentration of the stronger solvent to elute more strongly retained components. At the same time, the flow of the weaker solvent of the binary mixture is reduced to maintain a constant total flow rate.

Modern HPLC pumps frequently contain local controllers that allow download of the predetermined flow ramps form the system controllers. This frees the system controller from real-time control of the pumping system so that it can dedicate its effort to monitoring system status and detection signals and to provide a graphical display of results to users. A single start signal from the system controller initiates the downloaded instructions for the pump. Local controllers can sometimes even communicate among themselves to synchronize the pumping of complex ramps and to signal when an error state has occurred.

HPLC systems are generally designed to operate in the range of 0-400 bar of pressure and 0-10 mL/min total flow. This range is suitable for pumping aqueous-organic mixtures through separations columns with particles as small as 3 um with good separation quality. A major limiting design factor of these pumps is the maximum torque available to the drive motor.

In general, pump noise increases significantly in the last half of the pressure range for normal HPLC liquids. The compensating flow must increase to account for a larger flow lapse during compression. These flow/pressure variations translate directly to noise in the detector signal that can degrade detection limits, making both peak detection and quantitation difficult. Typical implementations of HPLC systems are insufficient to handle the requirements of SFC or ultrahigh performance LC where much larger compensating flows are required.

Figure 13:
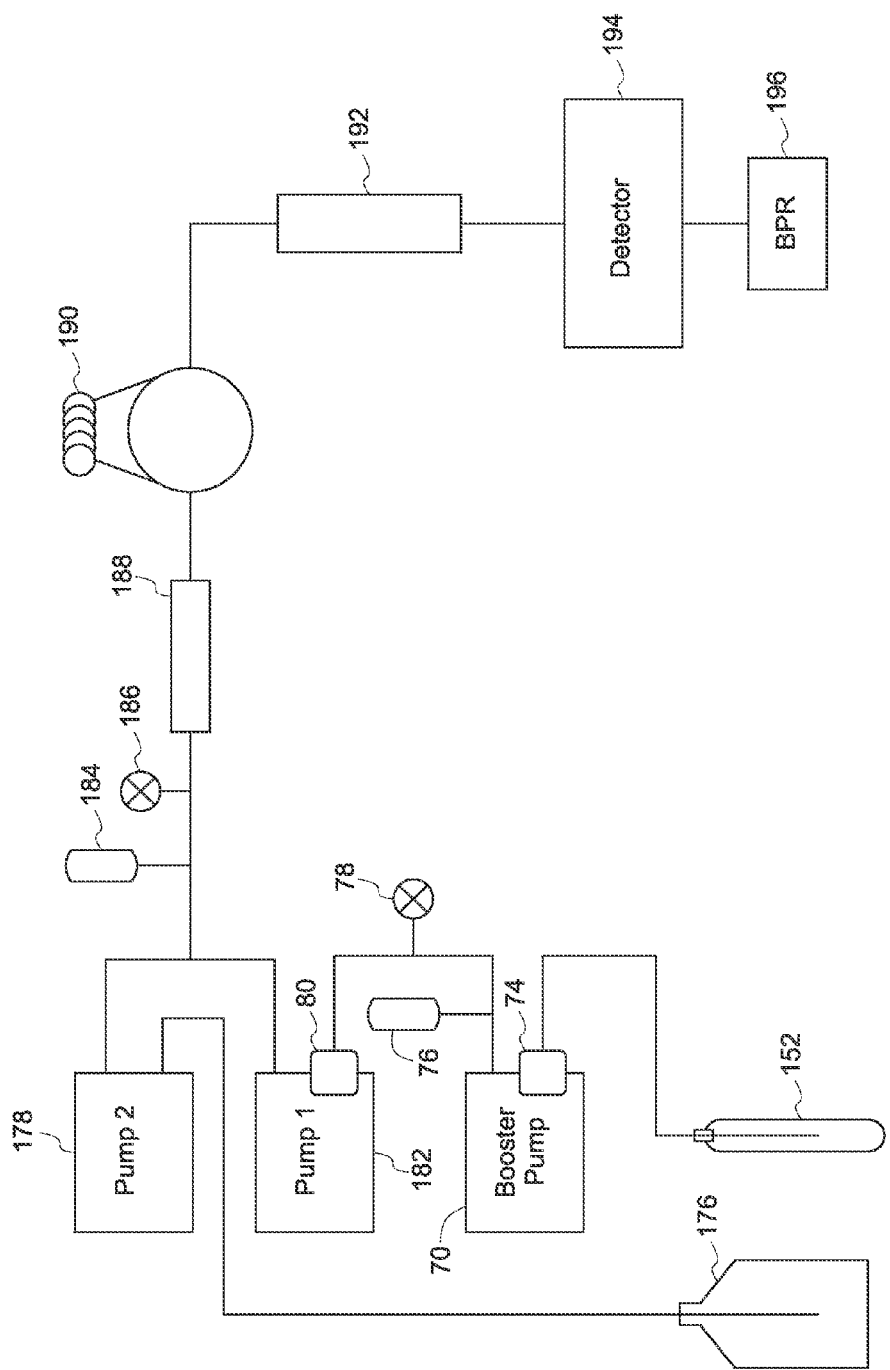
FIG. 13 illustrates an application of the preferred embodiment with a single compressible fluid in a high pressure chromatographic system.

Application of the preferred embodiment of the present invention in FIG. 13 demonstrates a method of converting the existing HPLC system in FIG. 12 to an SFC system. Addition of booster pump 70 with prechiller 74, pulse dampener 76, booster pressure sensor 78, and thermal conditioning device 80 to the system as well as a new local controller for these devices enables the previous HPLC system to perform under its normal control modes while pumping $CO_2$. In addition BPR 196 must be upgraded to an automated electromechanical BPR with at least 400 bar pressure regulation range and controlled by either controller.

Booster pump 70 receives its compressible fluid, such as a $CO_2$ supply, from reservoir 152 which is depicted as a high pressure cylinder. Other possible sources include liquid $CO_2$ from a cryogenic dewar, or from gas delivery system which converts low pressure gas to high pressure liquid $CO_2$ in the range of 70-100 bar. In addition, $CO_2$ vapor may be used it prechiller 74 has sufficient power to liquefy sufficient volumes to satisfy the booster pump flow demand.

In operation, the controller tracks the pressure of sensor 142 and adjusts the rate of booster 70 to control the pressure at sensor 78 to a level 1-10 bar lower. With a typical minimum operating pressure at BPR 196 of 100 bar and a maximum of 400 bar, booster pump 70 must be able to provide flow from 90-400 bar. The nominal flow rate of booster pump 70 should be at significantly greater than the maximum system flow to compensate for significantly lower density of the input fluid and for small leaks that may develop in the booster pump seals.

HPLC pump 182 is relegated to the metering role of the preferred embodiment. In this role, much of the compensation capability of the pump will go unutilized and may be reduced or deactivated depending on the pump. Further, due to the high pre-pressurization, pump 182 pumps against a very low pressure differential and requires much lower torque than its specification. The very low compression required means the flow lapse and subsequent compensating flow are virtually absent, making flow/pressure/detector noise much lower. Thus, even compressible fluids are delivered accurately with very low noise.

Few other system changes are required for successful conversion. The dynamic range of BPR 196 may require adjustment and it may be desirable to be converted to an active design with control from either a local or the system controller. Detector flow cells may require upgrade to higher pressure designs. In short, the original HPLC system is virtually unaltered and the conversion can be reversed easily if HPLC separations are required. Addition of one or more active switching valves to exchange the CO2 supply with a liquid supply respectively can make this conversion automatic and allow a dual-mode HPLC/SFC system without modification of the preferred embodiment.

Finally, implementation of the preferred embodiment into an HPLC system requires no change to the system controller of the original HPLC system. However it is preferred to pass control of setpoints of the preferred embodiment controller through the HPLC system user interface if possible.

The economic ramification of this application is quite large as it brings into practice the potential upgrade of a sizable fraction of the estimated 250,000 existing HPLC systems deployed in laboratory and process sites in industry and academia. Rather than obsoleting such equipment, it can be upgraded to SFC systems at much lower cost. Prevention from obsolescence also spares the older equipment from filling valuable landfill space which is an environmental benefit. Further, SFC is widely considered a "green technology" due to lower solvent use and waste generation compared to conventional HPLC. As a result it assists in lowering the "carbon footprint" of modern industry which has become of increasing political concern.

The SFC system depicted by FIG. 13 is scalable. Flow rates for traditional HPLC applications range from 0.5 to 2 mL/min. SFC flow rates are typically from 2 to 10 mL/min. Chromatography systems with much higher and much lower ranges exist for different applications. Packed capillary HPLC is a miniaturized form of the art that strives to reduce solvent utilization. The system typically uses single syringe pumps loaded with sufficient solvent for an entire elution. The technique would benefit from this invention by extending to include highly compressible fluids which would suffer significant compression during elution.

At the large scale, preparative chromatography systems deliver fluid from 20 to 2000 mL/min. These systems exist for both HPLC and SFC. Application of the preferred embodiment provides a system for developing analytical level methods that perform virtually identically on the larger systems. It further provides a localized technique via the thermal conditioning device 80 to deal with the significant amounts of thermal energy that needs to be dissipated. Utilization of this heat in the final evaporation stage of the $CO_2$ in the collection system could be used to great advantage. Other large preparative systems such as simulated moving bed [SMB] separators vitally depend on critical flow and timing to optimize effective separations. Mass flow modes of the preferred embodiment would be particularly useful in such systems.

Assembly of HPLC pump designs to an Ultrahigh Performance Chromatography System

Figure 14:
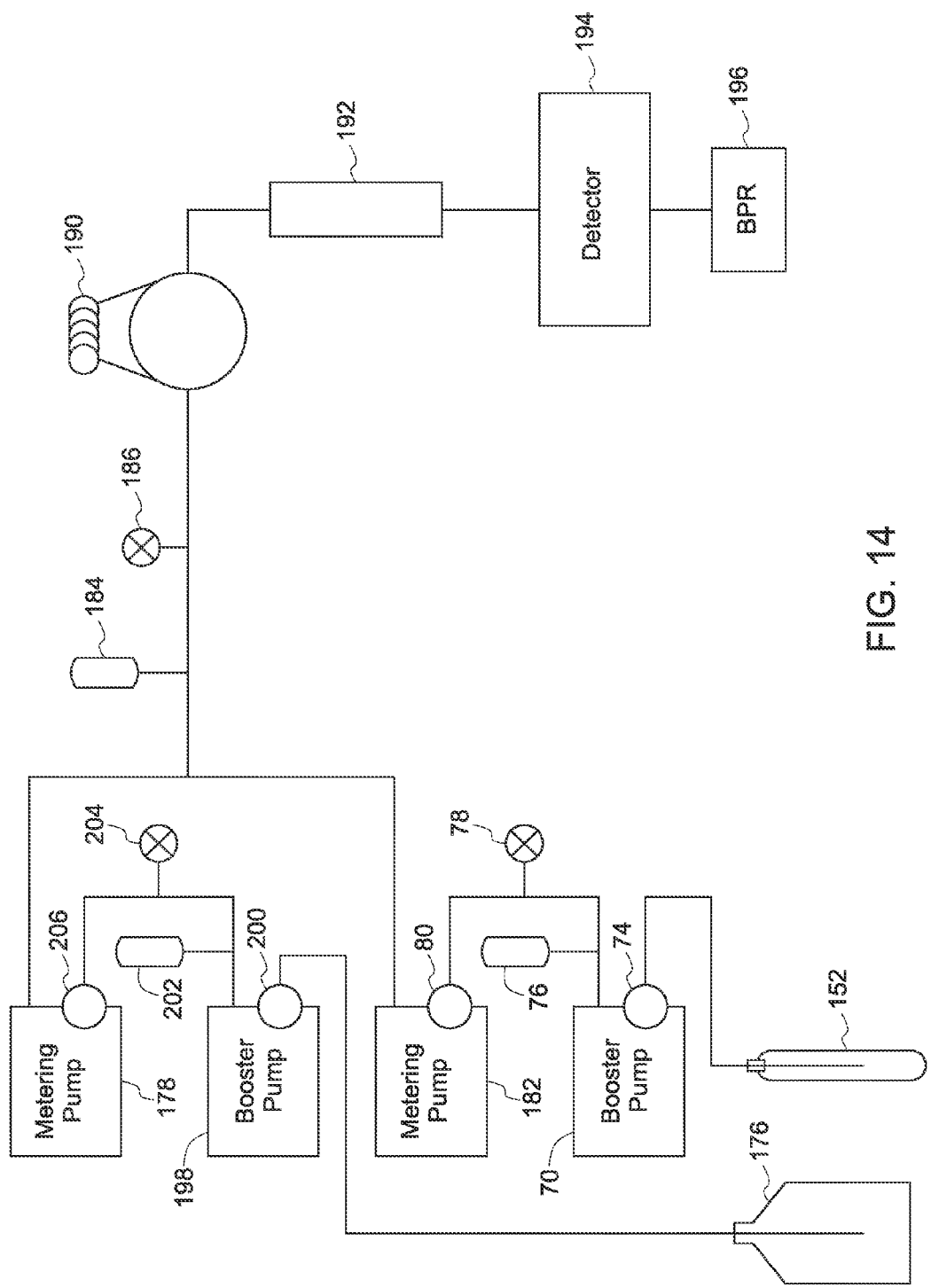
FIG. 14 illustrates an application of the preferred embodiment using multiple compressible fluids in a high pressure chromatographic system.

An additional alternative application of the preferred embodiment is shown in FIG. 14. In this case, a second booster pump 198 is added to support the second HPLC pump 178 in the system. Pulse dampener 202, pressure transducer 204 and thermal conditioning device 206 are also added to the system. The result is a new concept for the creation of ultra-high performance chromatographic systems which can operate up to 2000 bar.

Rather than simple extension of compression compensation using rapid compression strokes which do nothing to address adiabatic heating of the fluid, the preferred embodiment provides a clear means to handle heats of compression. This allows the ultrahigh pressure metering function to occur at a known state and eliminates the uncontrolled variable. Unmodified HPLC pumps may not be sufficient due to component specifications for maximum pressure. However, with upgrades of seals, sensors, tubing, and firmware, the basic designs of modern pumps is fully sufficient to reach very the high pressures required. Due to the low delta pressures of the invention, motor size may actually be reduced for metering applications, while improvements in piston drive stiffness may be required.

Figure 15:
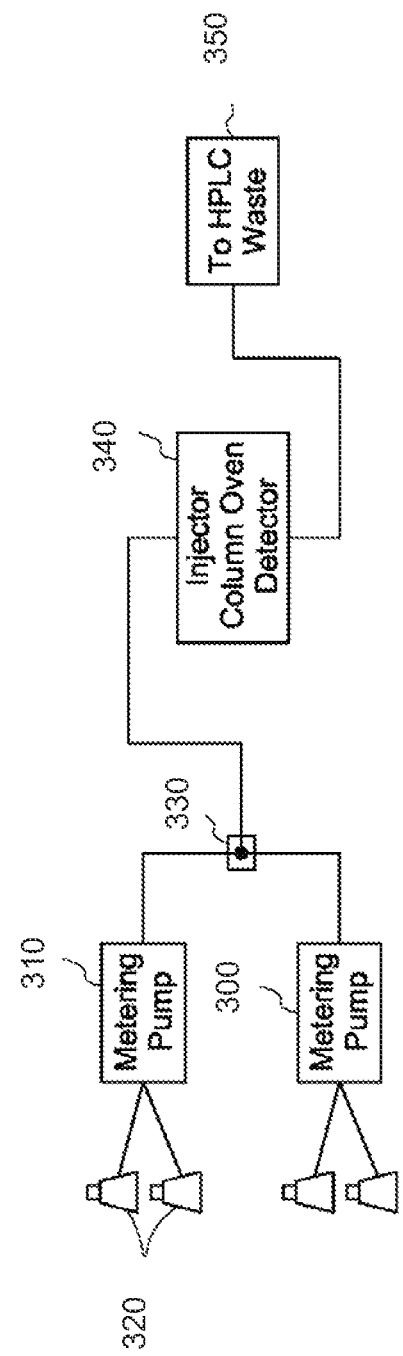
FIG. 15 illustrates a high pressure liquid chromatography system of the prior art using dual metering pumps.

A quick review of the different types of HPLC and SFC systems of prior art will assist in demonstrating common and opposing requirements of some prior art flow systems. FIG. 15 illustrates a flow path of a modern binary HPLC system of prior art. Two high pressure metering pumps 300 and 310 are used to create the mobile phase from solvent reservoirs such as reservoir 320 plumbed to the inlet of each pump. High pressure mixing is performed at mixer 330 positioned at or after the flow junction of the two high pressure outlet flow streams. The mixed flow proceeds through the modular flow system through components typically including a sample injection module, a separation column typically housed in a thermal control module or column oven and a detector. The serial collection of modules is depicted as instrument cluster 340 in FIG. 15 Finally after exiting instrument cluster 340, flow is directed to a waste container 350. The flow system is capable of isocratic or gradient elution chromatography for either reversed phase or normal phase HPLC; however normal phase HPLC is typically used only as a last resort owing to its very slow equilibration times and problems with reproducibility due to water adsorption. Not shown in FIG. 15 are various optional components including column selection valves, multiple detectors, manual injection valves and other items that may be used to customize the system. Similar omission of optional components is common in all described flow paths.

Figure 16:
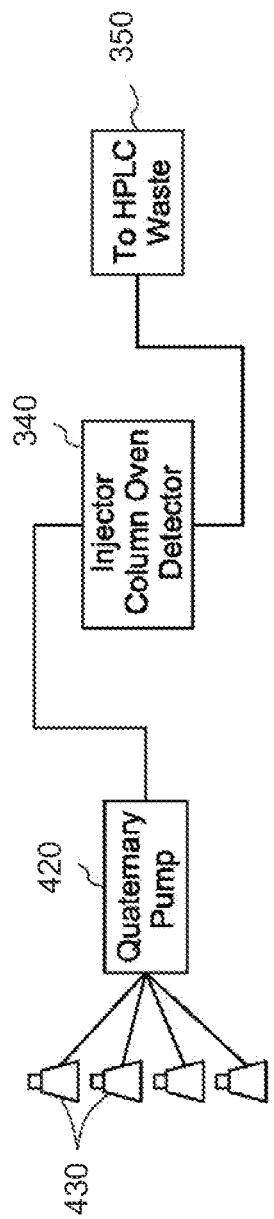
FIG. 16 illustrates a high pressure liquid chromatography system of the prior art using a quaternary pump.

FIG. 16 represents an alternative HPLC flow system using a single quaternary pump 420 to dynamically formulate specific mobile phase compositions. Pump 420 uses a low pressure proportioning valve to draw simultaneously from a bank of four solvent reservoirs 430 in varying ratios. The aspirated mixture is drawn through the pump heads and typically a pulse damper and or internal mixer completes the mixing process of the mobile phase. The pump delivers to module cluster 340 and the flow stream terminates in HPLC waste vessel 350 as described earlier. Because the internal dwell volume of quaternary systems tends to be larger and the individual components of the mobile phase are aspirated rather than pumped by positive displacement, quaternary HPLC systems are typically not considered as precise as binary systems in very highly demanding applications. However, such limitation is typically taken into account during method development and extreme performance demands such as very fast gradients or ultra high pressures are typically avoided. Under less stringent conditions, little difference is seen between low and high pressure mixing systems found in binary and quaternary system respectively. Like binary HPLC systems, quaternary flow systems are capable of isocratic or gradient elution chromatography for either reversed phase or normal phase HPLC with the same performance limitations in normal phase.

Figure 17:
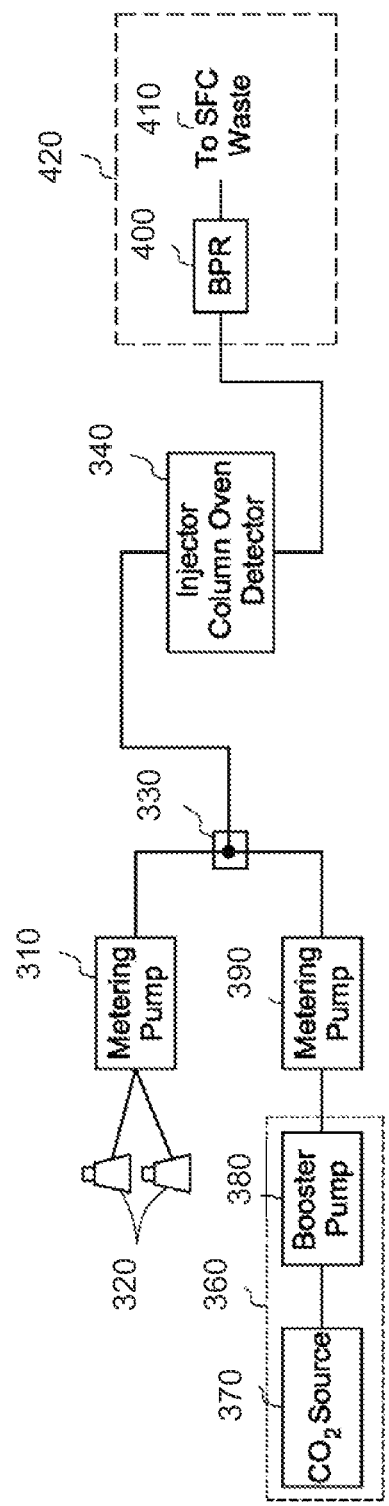
FIG. 17 illustrates an application of the preferred embodiment using multiple compressible fluids in a high pressure chromatographic system.

FIG. 17 illustrates a system that includes pump 310, high pressure mixer 330, and HPLC module cluster 340 which are essentially identical to those found in binary HPLC systems as illustrated in FIG. 15. For some types of HPLC modules, minor modifications are made such as converting injectors back to conventional sample loop injection modes or adapting detector cells for high pressure. New components in the SFC flow system include CO2 source 370, optional booster pump 380, CO2 metering pump 390, back pressure regulator (BPR) 400 and SFC waste container 410. The specialized equipment is required for the precise delivery of CO2 into the chromatographic system. Further, the mobile phase once mixed must be maintained at pressure generally above 80 bar to remain miscible. Since these pressures would otherwise be lost after the separation column, BPR 400 is required. Finally, custom waste container 410 is required that receives both expanded CO2 vapor and liquid organic modifiers and collects the liquid phase prior to venting. pSFC flow systems of the configuration of FIG. 17 are capable of isocratic or gradient elution chromatography generally for normal phase separations exclusively.

Highly pressurized CO2 is typically used in pSFC systems as the weak solvent for binary separations. Because of its high compressibility even in the liquid state, CO2 requires one or more flow enabling devices in order to be pumped precisely. Such flow enabling devices can include chillers, heat exchangers, booster pumps, and modified metering pumps as well as other devices. The requirements of booster pump 380 in FIG. 17 are highly dependent on the type of CO2 source connected. Older commercial systems did not require any booster if the CO2 was delivered from a liquid eductor tube of a high pressure liquid CO2 cylinder. Metering pump 390 took full responsibility for chilling, compressing and metering the CO2 as a liquid. When source 370 was a cryogenic dewar or storage tank, a booster pump 380 typically in the form of an air driven gas booster was required to bring the pressure up to a constant state that required less than a few hundred watts of power near zero ° C in order to bring the CO2 to a liquid state before pumping. Metering pump 390 remained responsible for final compression to the column pressure and CO2 metering functions.

Embodiments of a booster pump were previously described for the embodiments illustrated in FIGS. 4 to 14. In FIG. 17, booster pump 380 is modified to provide both chilling and dynamic precompression to a vapor phase inlet stream of CO2 between 40 and 70 bar. The pump liquefies the vapor stream and pumps it to a control pressure value directed at the inlet of metering pump 190 in a serial plumbing arrangement. The dynamic precompression is controlled by sensing the outlet pressure of pump 390 and remaining just a few bars below the sensed pressure regardless of pressure changes at the head of the column due to gradient elution. The effect of the invention is to enable conventional HPLC pumps to meter CO2 without further compression and with very little pump noise.

The SFC flow system of FIG. 17 is most similar to the binary HPLC system of FIG. 15. It uses high pressure mixing at mixer 330 to achieve precise composition in mobile phases. High pressure mixing is a requirement of SFC since CO2 at pressure less than approximately 80 bar are not miscible with significant amounts of organic liquid modifiers. Generally separations are carried out in SFC against column head pressures ranging from 100 bar to 400 bar, although with modern HPLC pumps, head pressures over 600 bar are achievable today. The generally high back pressure required by pSFC is typically not a problem since mobile phases using CO2 are generally between three and twenty times less viscous than aqueous mobile phases and so significantly less pressure drop occurs across the separation column. However, the presence of a high back pressure BPR could be an impediment when considering for use in a common flow path for both rHPLC or pSFC. Standard HPLC systems tend to expend all their pressure capacity just in overcoming flow resistance in the separation column.

A second difficulty lies with the specialization of CO2 boosters and pumps used in a dual mode system. It is obvious to one skilled in the art that the CO2 flow must be isolated from the main chromatographic flow path during rHPLC operation. Exposure of an HPLC mobile phase to pressurized CO2 would cause severe outgassing that interferes with all optical and most other detectors. Modern CO2 pumping systems also typically store a charge of highly pressurized CO2 in a reservoir within the flow system. Draining the stored CO2 by a sudden or unrestricted release of pressure is undesirable. Most CO2 pumping systems take some time to recharge to a level that is suitable for stabile chromatography so it is of advantage to maintain the pumping system in a charged state.

As mentioned above, pSFC is typically considered a normal phase technique although niche applications have used C18 and cyano stationary phases with high polarity modifiers. Since CO2 at liquid-like densities has a polarity approximating hexane, it does not substantially dissolve water except as an additive to other more soluble organic modifiers. Nor do CO2 mobile phases tolerate ionized compounds, again except as supported by the polar organic modifiers used in the mobile phase. Further ionic species tend to accumulate strongly on the polar stationary phases and do not elute leading to loss of column efficiency and eventual flow blockage. This is in direct conflict with the use of ionized buffers in HPLC to control speciation of polar compounds. Significant care must be taken to rinse common flow paths in chromatographic systems that can switch between pSFC and rHPLC applications to prevent outright precipitation of residual buffers in the flow lines or the columns due to mobile phase incompatibility.

There is an unmet demand for a method and device for rapidly switching between the rHPLC and pSFC modes in a common instrumentation configuration. The two techniques are complimentary with opposing separation mechanisms. Hence if a separation fails or is very long in one mode, it will likely succeed and or shorten in the other. Such a system further diminishes the concern of dedicating a system fully to a less familiar technique such as SFC for the main stream of users. Ideally, the method uses the same high pressure pumps for both modes of operation rather than different banks for each mode. Finally, there is a significant economic driver of being able to share expensive components such as mass spectrometers or electronic light scattering detectors (ELSD's) between modes, dramatically improving the confidence in the separation in both modes.

Care must be taken in any dual mode system to insure full conversion of flow paths between modes and adequate rinsing capability of common flow paths. Further, overall utility of the system requires that CO2 subsystems remain charged in a safe manner during rHPLC separations for rapid reconversion to SFC modes.

Figure 18A:
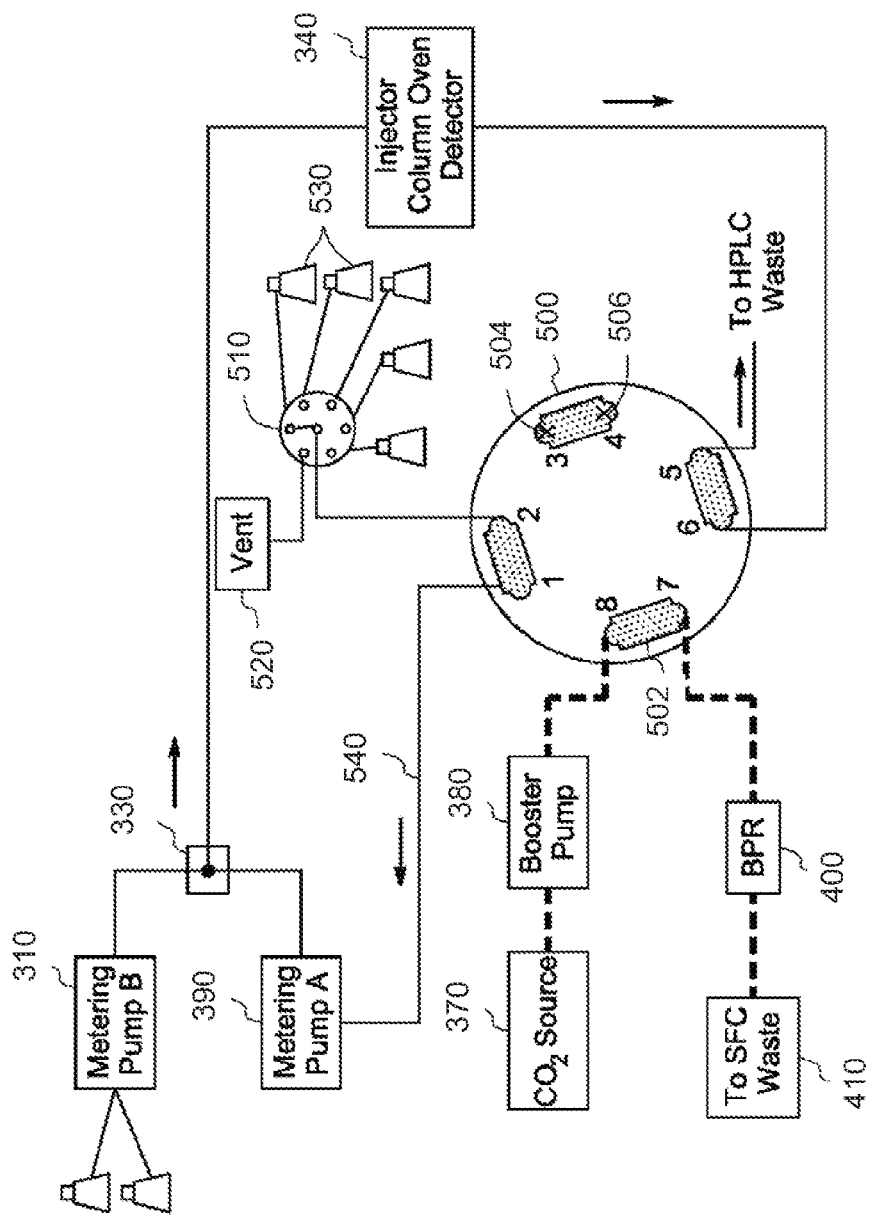
FIGS. 18A and 18B illustrate the two valve states of an 8-port valve arrangement enabling conversion between binary HPLC and binary SFC.
Figure 18B:
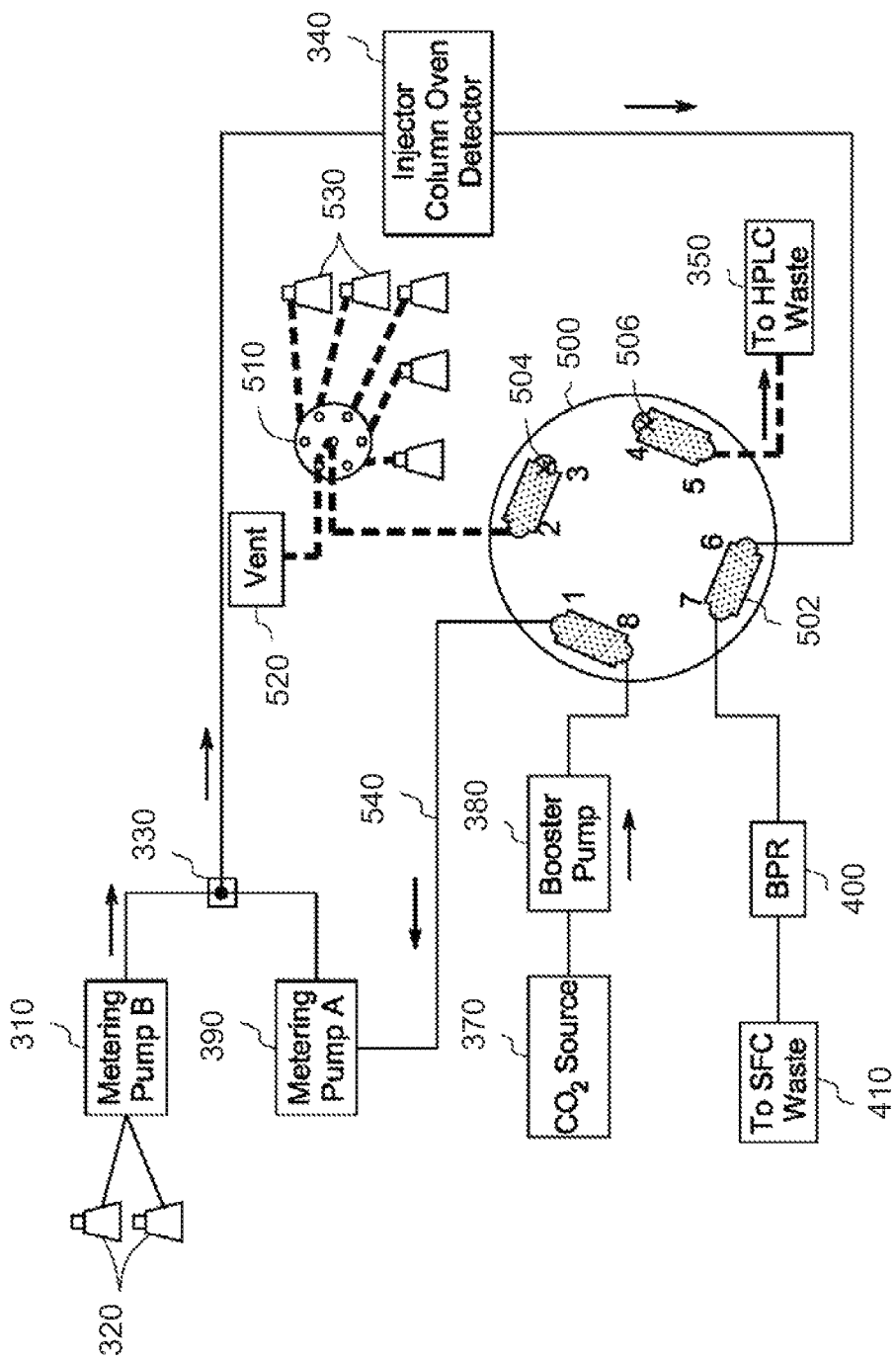

Other embodiments of the invention that relate to a binary HPLC pumping system are illustrated in FIGS. 18A and 18B. Functional system diagrams in FIGS. 18A and 18B display the two unique positions of 8-port switching valve 500. Fluidically connected valve positions 502 are numbered one through eight in the figures. Each figure shows 1) the valve arrangement connections to various modules of the HPLC or SFC flow system respectively; 2) the primary flow path demarked by flow arrows and 3) the secondary flow path or paths marked with dotted flow lines. Although variations of a multi-port selection valve are shown and described in the embodiments, one skilled in the art will appreciate that the device and process used to selective switch or change flow paths in the present invention is not limited to a multi-port valve or use of such a valve; other devices and processes could be arranged that can switch flowstreams such as automatic electronic switches, manual switches or valves without departing from the scope or intent of the claims of the present invention.

The system embodied in FIG. 18A represents the valve position in its binary HPLC mode. In this valve position, solvent selection valve 510 is used as a liquid solvent inlet to pump 390 to provide both a variety of suitable solvents 530 for the HPLC process. One position of solvent selection valve 510 is reserved for connection to vent 520 which is used to drain the small volume of CO2 based mobile phase trapped in line 540 when valve 500 is switched. Venting is performed to insure solvents can be primed into the inlet of metering pump 390 with relative ease. Pump 390 is a conventional HPLC or UHPLC pump modifier for high pressure input and capable of pumping either CO2 or HPLC type fluids. In this latter mode pump 390 is equivalent to pump 300 of FIG. 15. Similarly, Pump 310 typically will pump water during HPLC separations and is identical to the pump 310 of FIG. 15. In this configuration, HPLC mobile phases are created by mixing the outputs of pumps 390 and 310 through mixer 330; directing the mobile phase liquids through instrument cluster 340 which performs the HPLC separation and flowing on to HPLC waste 350 which accumulates the spent mobile phase. As a result, FIG. 18A provides a fully implemented high pressure mixing binary HPLC mode similar to FIG. 15. Mixer 330 is comprised of mixing elements known in the art or anticipated devices which enable the mixing of two or more flow streams to near homogeneity within delay volumes practical for chromatography. It should be noted that the secondary flow path which includes CO2 source 370, CO2 booster 380, BPR 200, and SFC waste 401 maintains communication between the charges CO2 supply sub system and the vented BPR. As such, the supply subsystem may be maintained safely at full charge and ready to deliver when the SFC mode is engaged.

Switching valve 500 to its alternate position creates a new flow path configuration that enables an SFC mode of operation as illustrated in FIG. 18B. In this configuration, the main flow path is suitable for binary SFC as depicted in FIG. 17. CO2 booster pump 380 becomes the sole supply to metering pump 390 transforming this side of the pumping system for CO2 delivery. Metering pump 310 is switched to a suitable organic solvent modifier miscible with CO2 such as methanol. BPR 400 connects to the detector outlet from instrument cluster 340 and completes the requirement for back pressure control. Selection valve 330 and HPLC waste container 350 as secondary paths are isolated by plugs 504 and 506 respectively to prevent uncontrolled siphoning while not in use.

Certain considerations must be taken when switching between valve positions of FIGS. 18A and 18B. When switching from HPLC mode to SFC mode, pump 310 will be pumping water and pump 390 will be pumping the solvent selected from valve 510. As a precaution, the entire HPLC flow system should be rinsed with a solvent compatible with both water and CO2 such an alcohol. Typically users will have prepared switchover methods in the controlling workstation to accomplish this task. In cases where aqueous buffers are used, a rinse with water first then organic solvent should be implemented. Hence at the switching point of the valve, the entire system is primed with compatible solvent. Also at this time it will likely be appropriate to select the column to be used in the SFC mode and rinse it with solvent as well. $CO_2$ is pre-pressurized and is self-priming. That is, the pressure of the $CO_2$ from booster 380 is sufficient to force residual solvent from flow line 540 through pump 390 and allow pumping of $CO_2$ from pump 390.

Switching valve 500 from SFC mode enables HPLC mode. First valve 510 is selects vent 520 as its flow path. Valve 500 is switched to the position in FIG. 18A and residual pressurized $CO_2$ is vented from flow line 540. Valve 510 the selects an appropriate rinsing solvent and Pump 390 is primed. Automatic priming may require use of an automated prime valve, not shown to allow the organic solvent to fill flow line 540. An appropriate HPLC column is selected and the flow system is primed with neutral organic solvent. Pump 310 is switched to water and then any specialized aqueous buffer and the system is ready for HPLC separations.

Figure 19A:
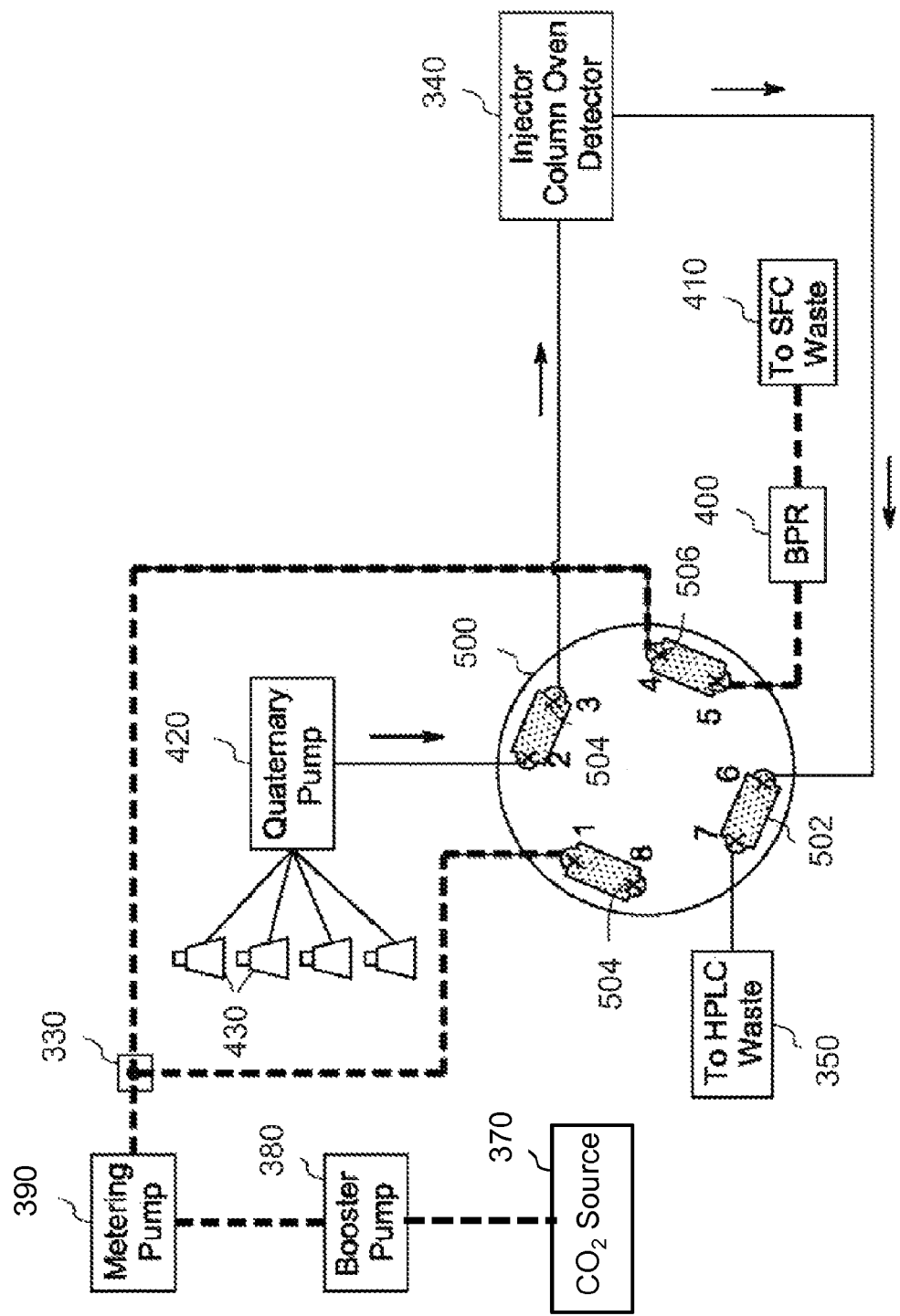
FIGS. 19A and 19B illustrate two valve states of an 8-port valve arrangement enabling conversion between quaternary HPLC and binary SFC with custom modifier composition.
Figure 19B:
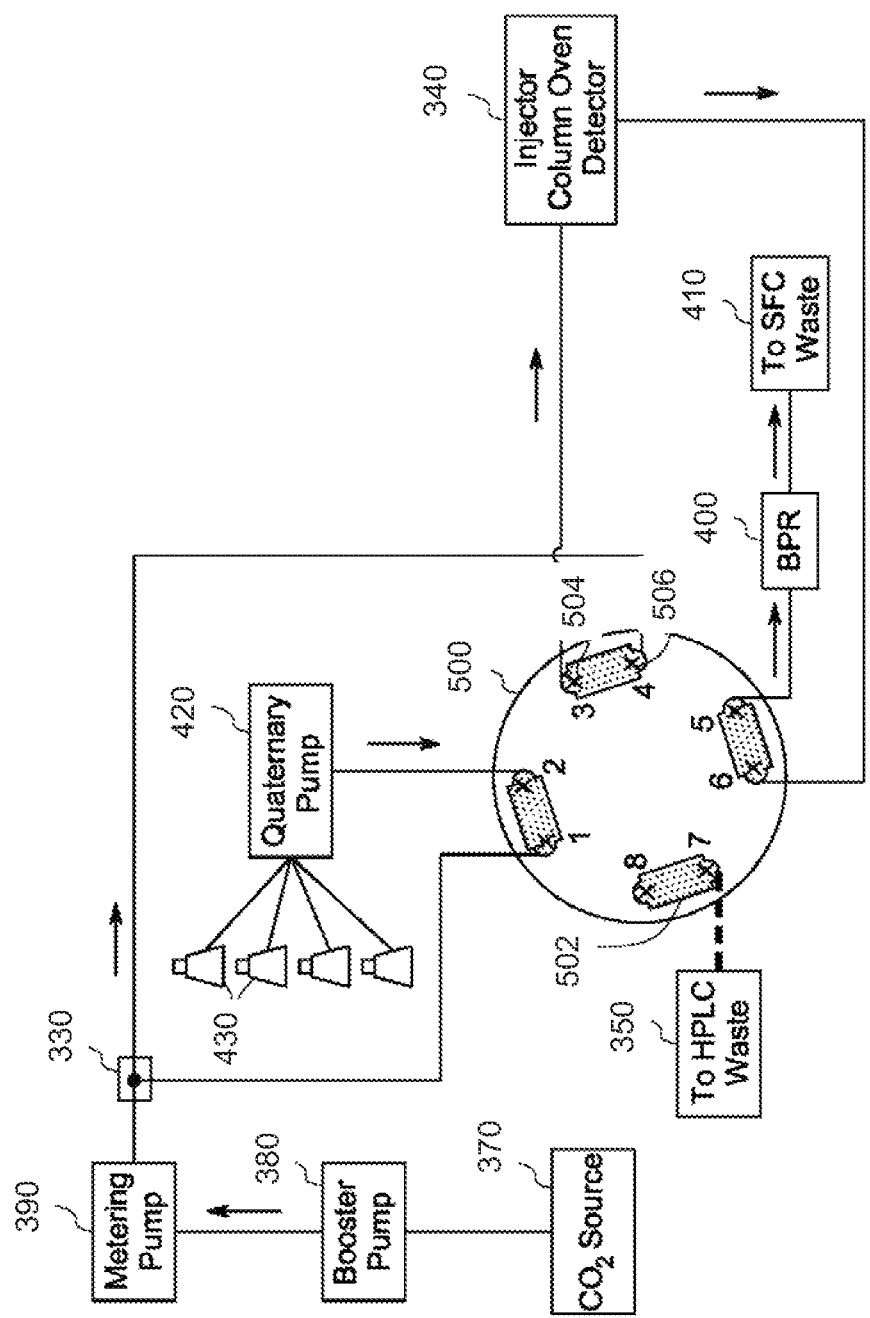
Figure 20:
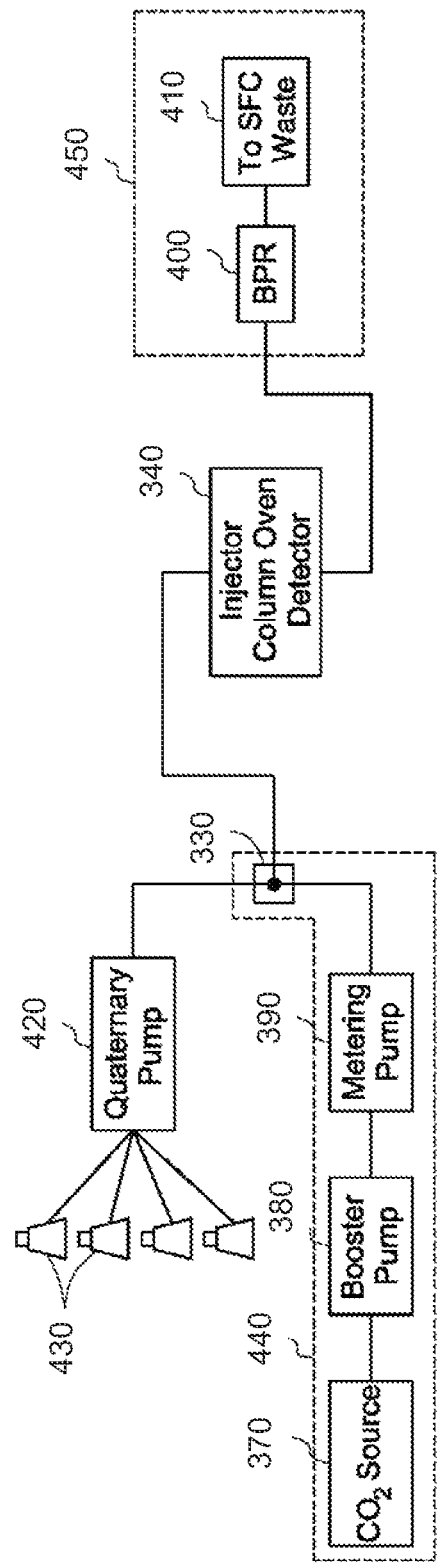
FIG. 20 illustrates the flow path of a modified binary SFC system using a quaternary pump to supply custom modifier compositions as in FIG. 16B.
Figure 21:
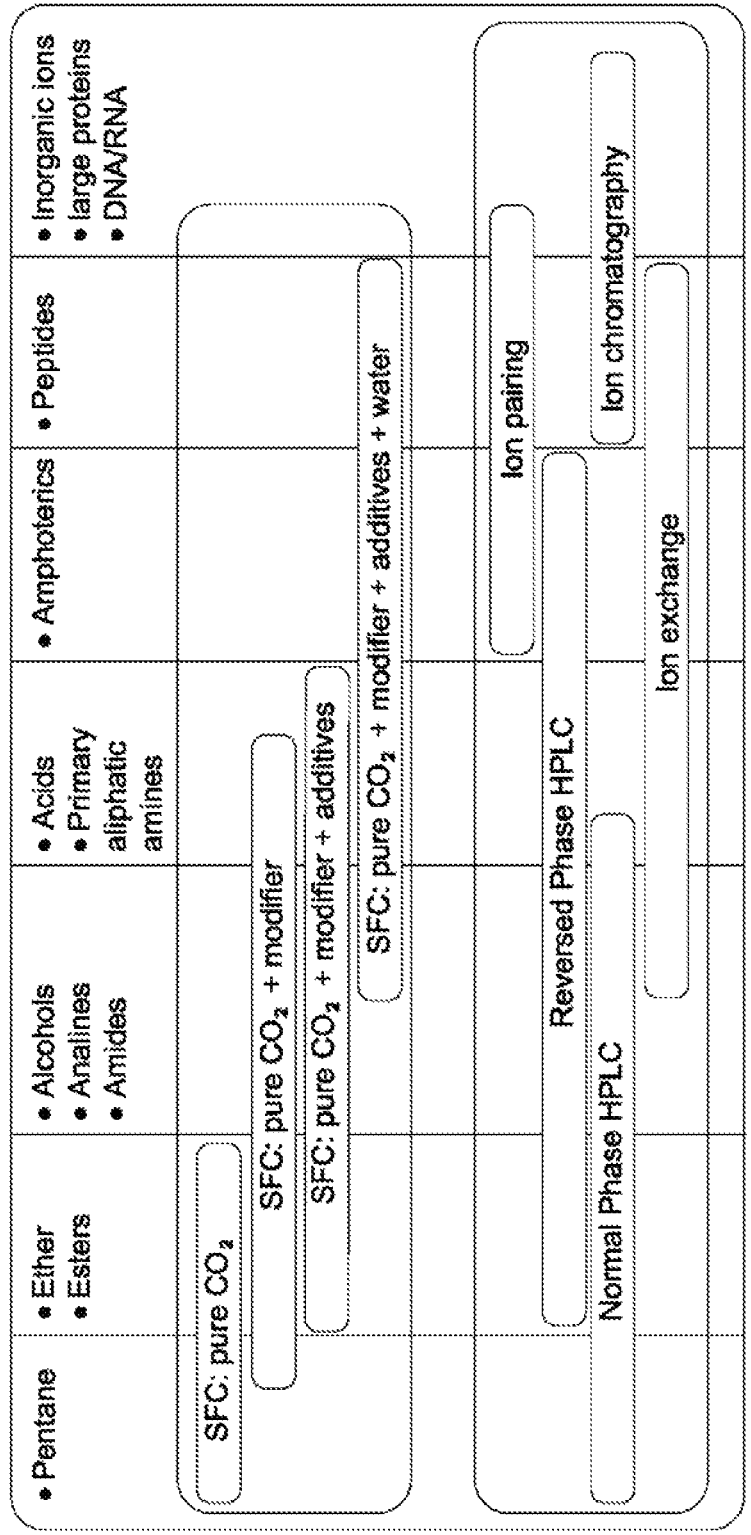
FIG. 21 is a chart showing the effect of varying modifier composition on range of analytes separated by SFC.

FIGS. 19A and 19B illustrate an alternate embodiment of the invention wherein an 8-port valve configuration allows switching between a quaternary HPLC flow path with low pressure mixing and a binary SFC flow path with low pressure mixing of modifiers and high pressure mixing of $CO_2$ and modifier. In FIG. 19A, the primary chromatographic flow path is highlighted with arrows. This flow path combines quaternary pump 420 with reservoirs 430 with instrument cluster 340 and HPLC waste container 350 as described in FIG. 16, above. Meanwhile the secondary flow path maintains $CO_2$ metering pump 390 in communication with BPR 400 in such a manner the $CO_2$ pumping subsystem can remain charged with the BPR supplying a safe venting path against overpressurization FIG. 19B represents a new advance in the art of SFC. In this configuration, the flow system resembles that of FIG. 17 with simple high pressure mixing at mixer 330. A major difference, however, exists in this configuration. FIG. 20 displays a schematic of the new flow path where quaternary pump 420 with reservoirs 430 replace the isocratic metering pump 310 if FIG. 17. Hence, the user is able to select from a near infinite number of combinations of modifier compositions to combine with $CO_2$ for the SFC separation. FIG. 21 demonstrates the high importance of this feature. SFC is a dynamic art with continuous advances in its range of separation utility. FIG. 21 shows a chart of the effective range of analysis of SFC in combination with varying compositions of modifiers. The original concept of SFC is shown first where pure $CO_2$ was used as a modifier with a tunable solvating power based on the $CO_2$ density. It was soon realized that addition of organic liquid modifiers dramatically extended the analyte range and shifted the emphasis from GC to LC like separations. Further extension of the techniques has been realized by addition of small quantities of acids or bases, called additives, the organic modifiers to control ionic speciation and compete with active sites on the stationary phase. Water has also been used as an additive typically to alcohol modifiers to enhance solubility of more polar species. The result of changing modifier composition has been to increase the effective range of SFC beyond that currently practiced by the sum of normal phase and reversed phase HPLC in total. As a result, an SFC system that can programmatically call up various combinations of modifiers and additives in varying compositions contributes greatly to the art.

Such ability is not without limitations. As described earlier, quaternary pumps typically contain a large internal delay volume arising from internal pulse dampers and mixer elements not shown in FIG. 20. Such delay volumes can range from hundreds to thousands of microliters. The presence of large delay volumes significantly separates the timing between changes in flow and changes of composition of flow coming from the quaternary pump. For example, if the delay volume were assumed to be 1000 uL, and the quaternary flow rate were 0.5 mL/min [500 uL/min] it would take two minutes before a change in the composition reached mixer 330. One the other hand, changes of total flow occur virtually instantly at the mixing point and at the same time alter the delay time between the modifier mixing point in the quaternary pump and mixer 330. In gradient elution chromatography, it is common to continuously chance the volumetric ratio of strong and weak solvents. In SFC this refers to modifier and $CO_2$ respectively. This implies that typical SFC method will require a change in the flow rate coming from quaternary pump 420 during gradient elution. While the user may also wish to vary the modifier composition during this time, it is quite difficult, due to the large and variable time delay of the composition change in the flow system, to track what the flow and composition entering the column at any time. Conditions will also vary significantly as a function of the gradient rate and total SFC flow rates. As a result, users are not encouraged not to try varying both parameters. Instead the benefit of a single composition of modifier per run varying in flow rate remains very high, and allowing the composition to change between runs for subsequent analyses remains available.

Figure 22A:
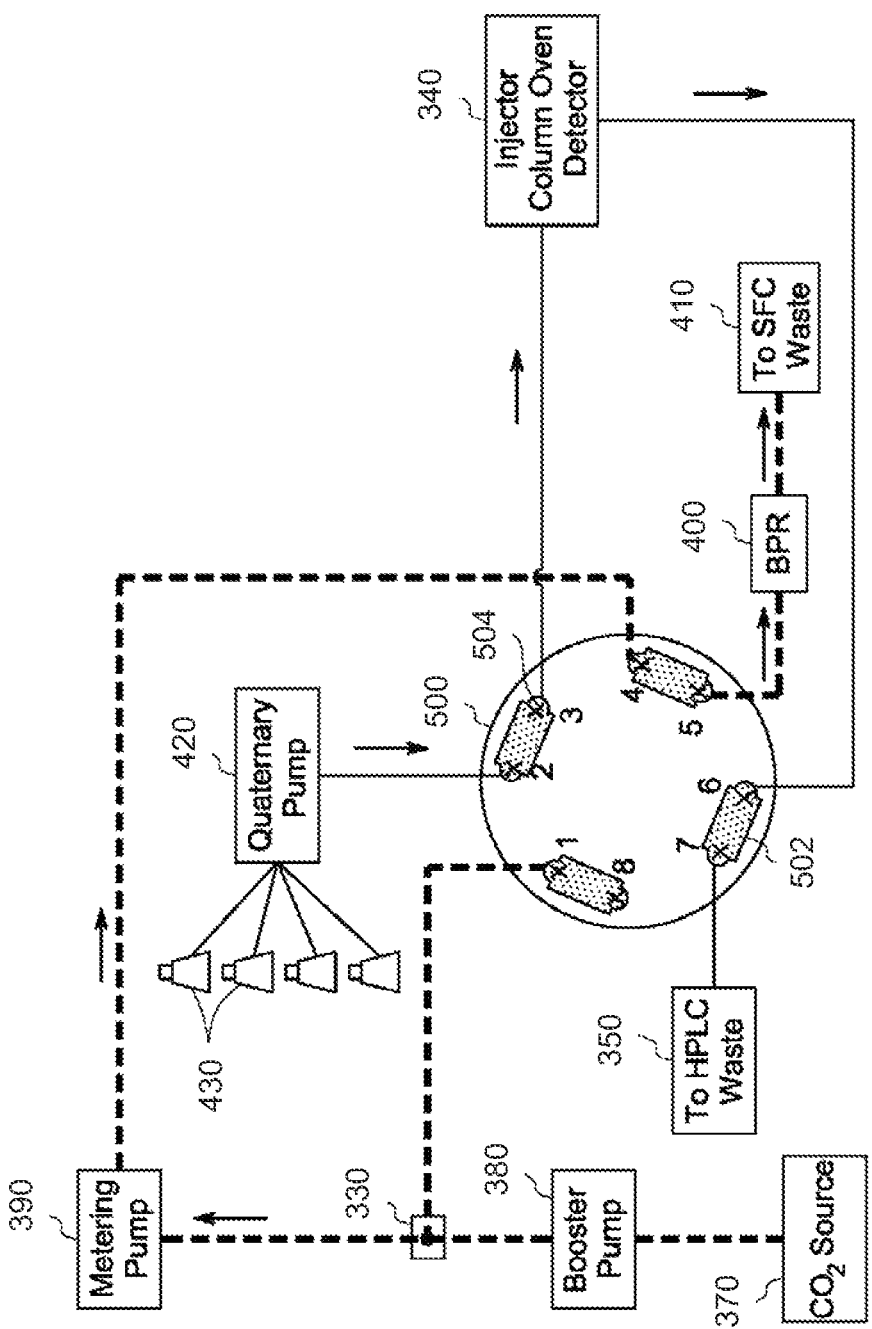
FIGS. 22A and 22B illustrate two valve states of an 8-port valve arrangement enabling conversion between quaternary HPLC and modified binary SFC with custom modifier and premixing with a high pressure CO2 stream prior to a metering pump supplying accurate total flow.
Figure 22B:
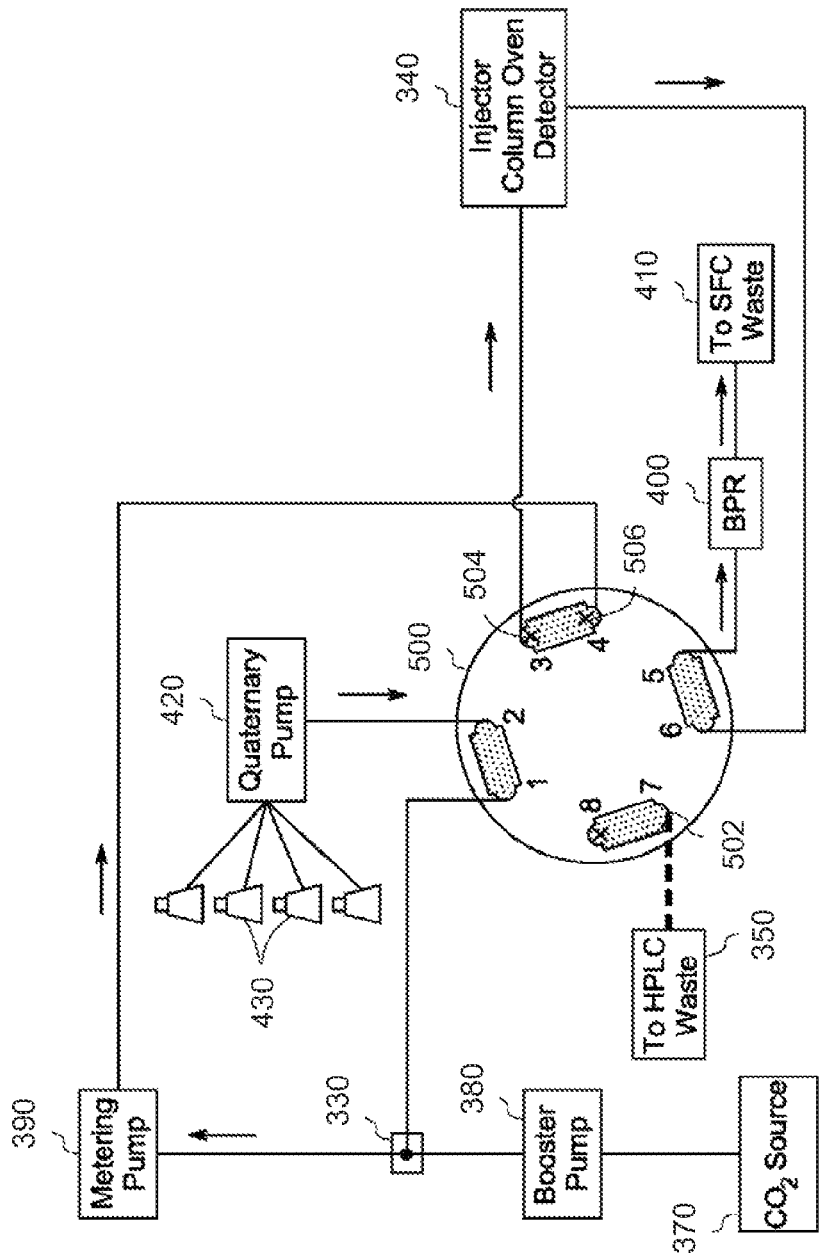

FIGS. 22A and 22B illustrate another alternate embodiment of the invention wherein an 8-port valve configuration allows switching between a quaternary HPLC flow path with low pressure mixing and a binary SFC flow path with low pressure mixing of modifiers and high pressure mixing of $CO_2$ and modifier. In this case, the high pressure mixing step occurs prior to pump 390 which now meters total flow rather than only $CO_2$ flow. A description of this so-called quantitative solvation method of mixing has recently been submitted as a patent application to the US Patent office. In FIG. 22A, as in FIG. 19A the primary path is that of a quaternary HPLC of prior art, while the secondary path connects the $CO_2$ pumping subsystem to the BPR and waste as described earlier.

Figure 23:
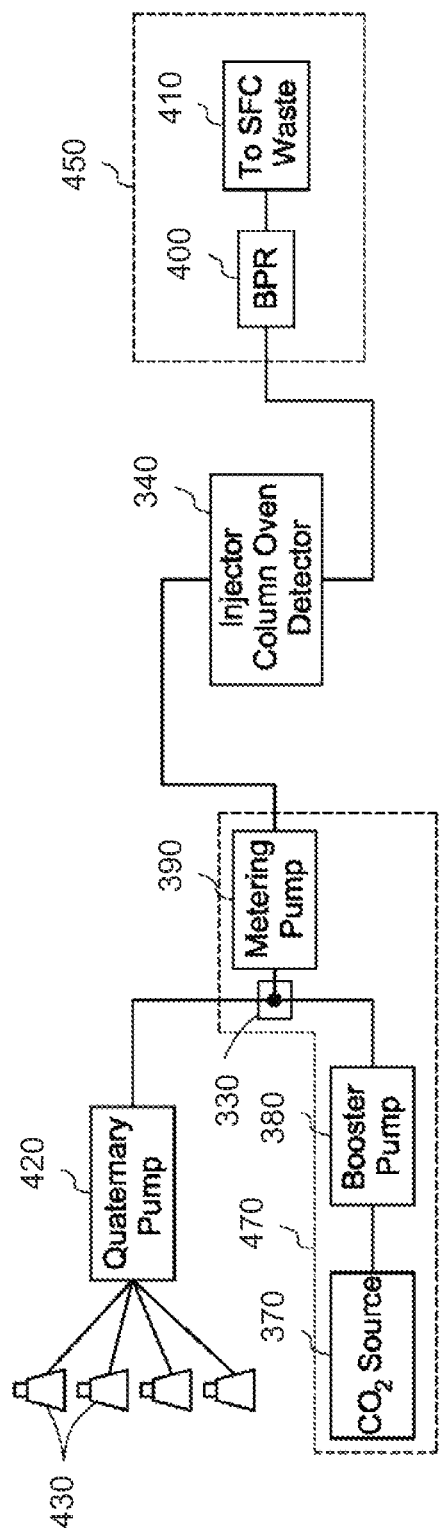
FIG. 23 is an illustration of a flow path of a modified binary SFC system using a quaternary pump to supply custom modifier compositions and premixing with a high pressure CO2 stream prior to a metering pump supplying accurate total flow as in FIG. 19B.

Unique in this embodiment is the ability to switch to the flow configuration of FIG. 22B which enjoys the advantages described for FIG. 19B when using a quaternary pump as the modifier generator as well as the stated limitations. In addition, the configuration allows the $CO_2$ to go unmetered but rather simply to complete the total flow demand of metering pump 390 not delivered as modifier by quaternary pump 420. FIG. 23 illustrates the details of the flow path. Booster pump 380 elevates the pressure of $CO_2$ from $CO_2$ source 370 to just below the outlet pressure of pump 390. Quaternary pump 420 delivers a flowstream less than or equal to the volumetric flow rate of metering pump 390 which determines total flow for the chromatographic separation. When the volumetric flow of pump 420 matches the rate of pump 390, little or no $CO_2$ is delivered to the final mobile phase except what may dissolve into the modifier under pressure. When the modifier flow is less than the total flow demand of pump 390, sufficient $CO_2$ is delivered to complete the demand. Typical gradient runs in SFC general span compositions of 5% to 60% modifier. Thus in normal operation, $CO_2$ volumetric delivery represents 40% to 95% of the total flow plus any $CO_2$ required to make up for losses due to mixing. Flow continues through instrument cluster 340 and BPR 400 as stated in earlier configurations.

This arrangement has two major advantages. First, it provides a more controlled volumetric flow rate into instrument cluster 340 since volumetric losses from high pressure mixing in mixer 330 are made up by additional CO2. Second because booster 380 dynamically precompresses the mobile phase mixture before metering through metering pump 390, compressibility changes in the gradient mobile phase do not result in variable higher pump noise. Mobile phases generated by the configuration of FIG. 22B are more compositionally accurate regarding the strong solvent of the separation.

Figure 24A:
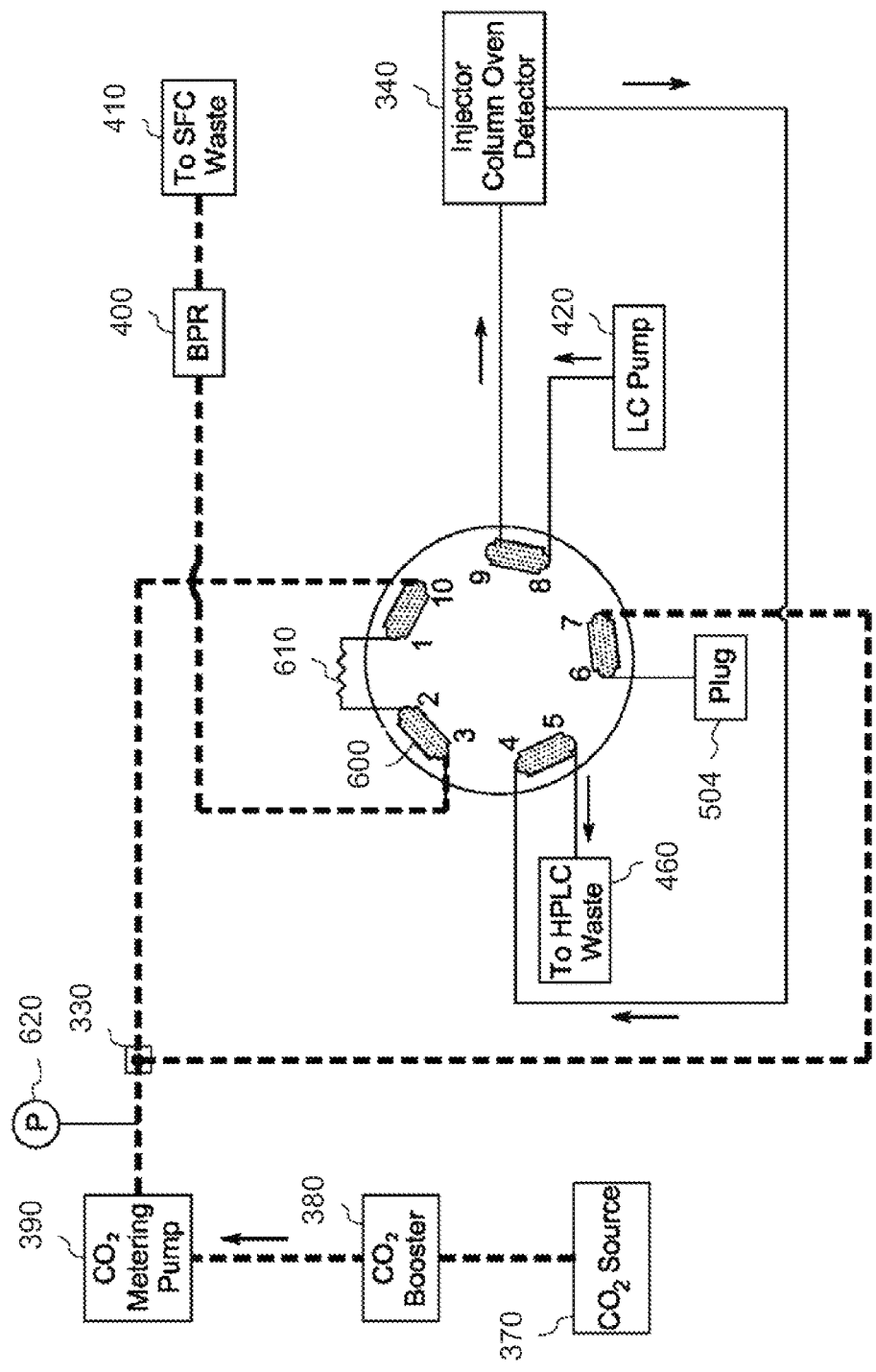
FIGS. 24A and 24B depict the two valve states of a 10-port valve arrangement enabling conversion between quaternary HPLC and modified binary SFC with custom modifier composition.
Figure 24B:
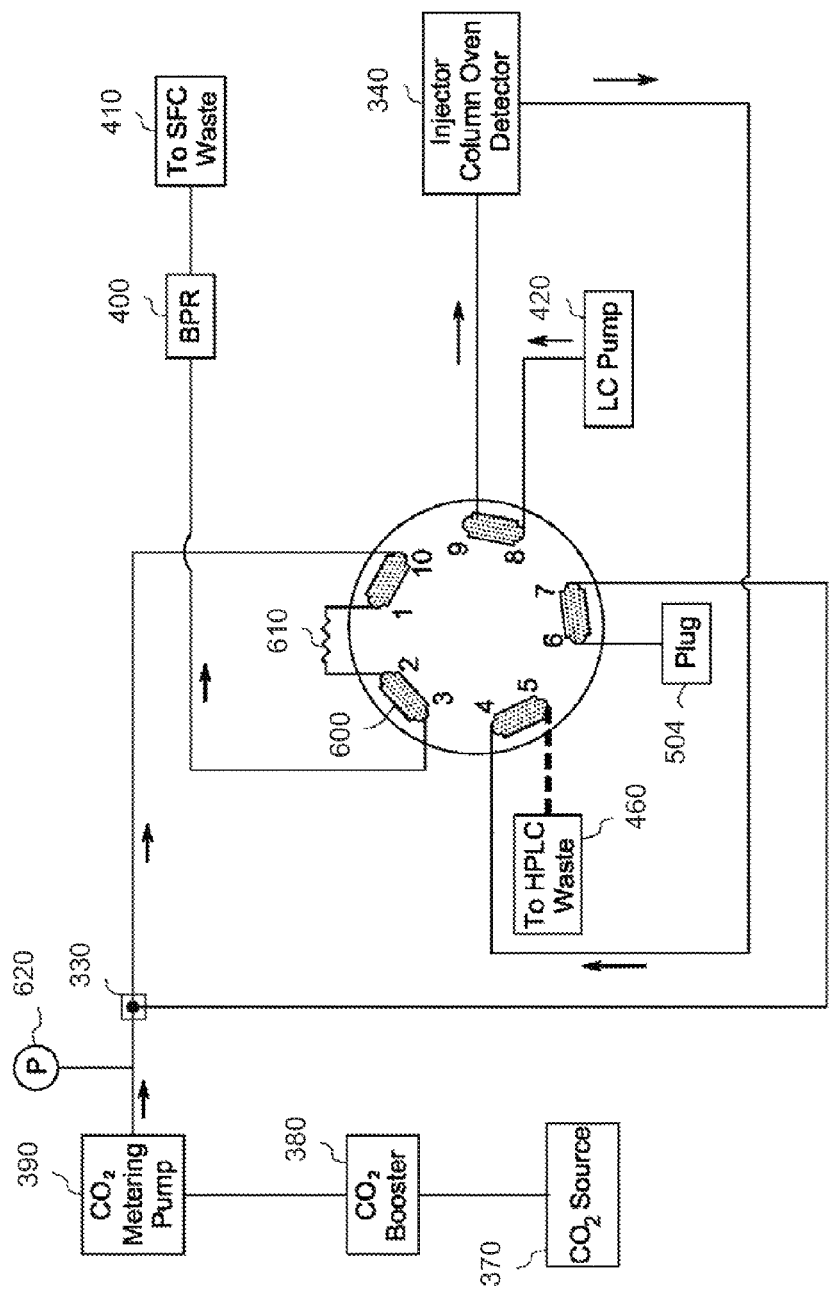

Embodiments of the invention can be implemented by other than 8-port valves. FIGS. 24A and 24B illustrate an alternate embodiment of the invention wherein a 10-port valve configuration allows switching between a quaternary HPLC flow path with low pressure mixing and a binary SFC flow path with low pressure mixing of modifiers and high pressure mixing of CO2 and modifier. In these figures, the primary path is indicated by arrows and solid flow lines. The secondary path is indicated by dotted flow lines. FIGS. 24A and 24B add new elements of 10-port valve 600 and flow restrictor 610. The valve can be any 10-port high pressure switching valve with an upper pressure of at least 5000 psi. Flow restrictor 610 is typically a reduced I.D. flow capillary with appropriate flexibility and length sufficient to connect to two adjacent ports of the valve. Restrictor 610 serves as a flow channel to complete the secondary fluidic path of FIG. 24A. It has the beneficial added use of providing a resistive diagnostic flow path for the CO2 delivery subsystem under simulated conditions of flow between pump 390 and BPR 400.

In FIG. 24A, as in FIG. 19A, the primary path is that of a quaternary HPLC of prior art, while the secondary path connects the CO2 pumping subsystem to the BPR 400 and waste container 410 as described earlier. The one difference as noted is the inclusion of restrictor 610 in the flow path which allows simulation of metered flow similar to flow through a column for diagnostic purposes. FIG. 24B recreates the SFC mode flow path illustrated in FIG. 23 which has already been described. In this flow path, restrictor 610 is isolated from the rest of the flow stream. Pressure sensor 620 is included in the flow stream as an exemplary means of creating the pressure signal used by booster 380 in certain configurations of the CO2 pumping subsystem. The positioning of pressure sensor 620 is also exemplary as it could be located at any point along the flow stream prior to instrument cluster 340 so long as an insignificant pressure drop occurs between the pump outlet and the sensing point. Positioning in the pure CO2 flow stream is preferred, however, since CO2 is less corrosive than some organic modifiers and additives used in SFC.

Figure 25A:
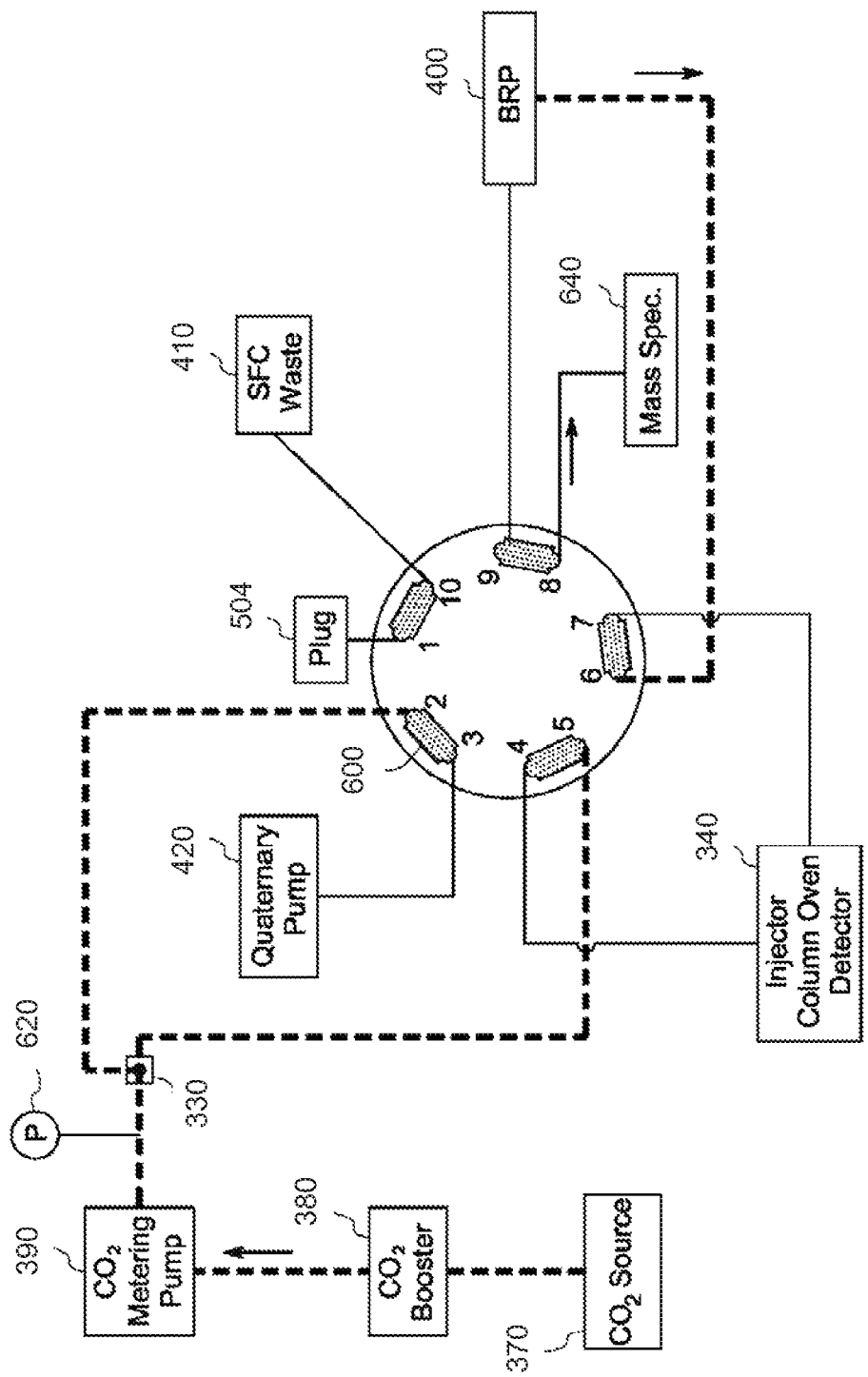
FIGS. 25A and 25B depict the two valve states of a 10-port valve arrangement enabling conversion between quaternary HPLC and modified binary SFC with custom modifier composition and delivering flow to a mass spectrometer.
Figure 25B:
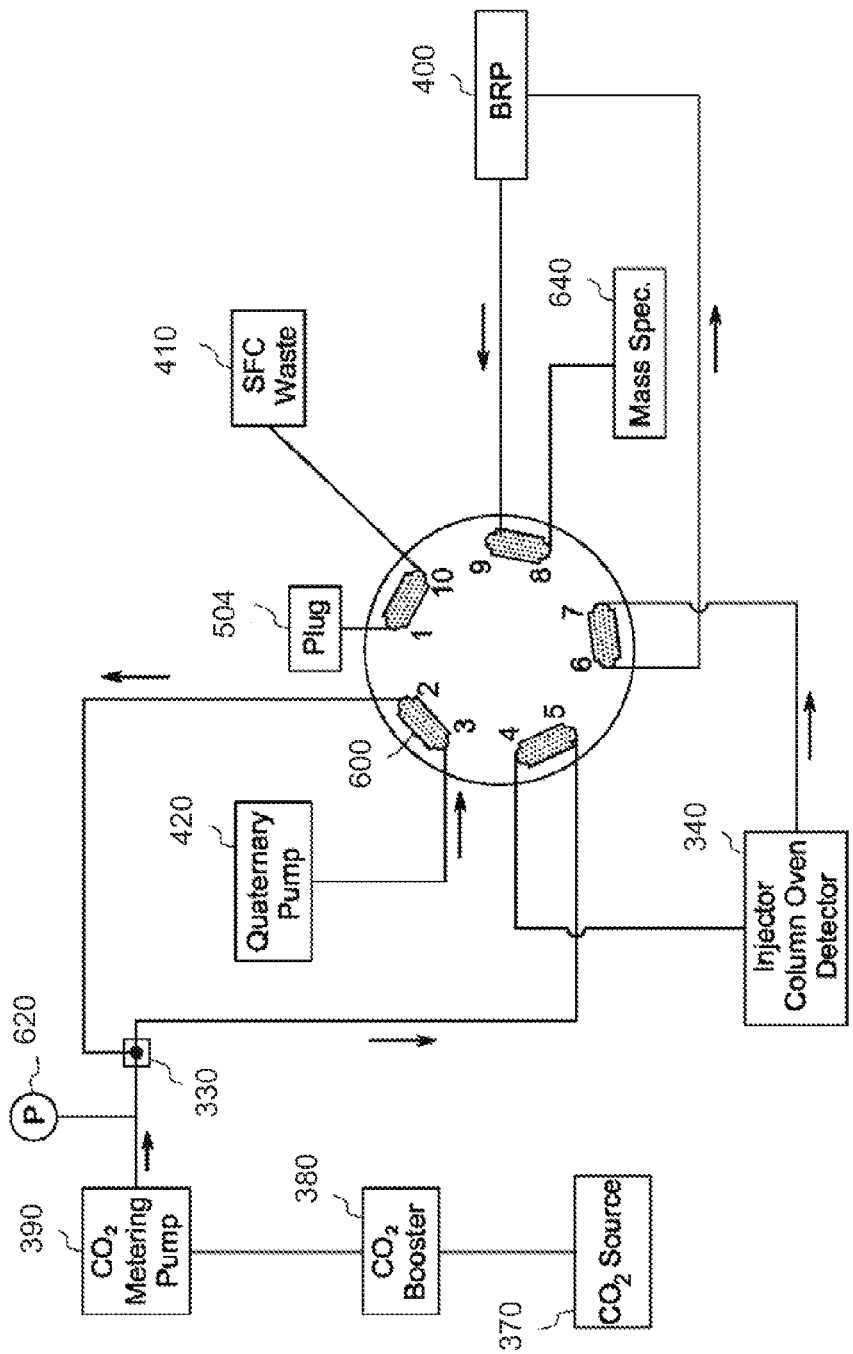
Figure 26A:
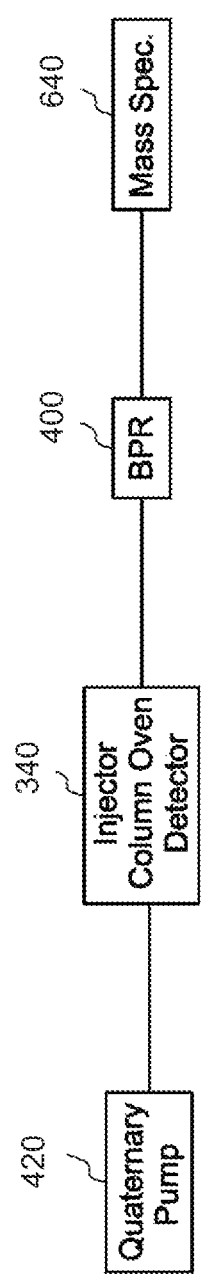
FIGS. 26A and 26B depict the two flow paths created by the valve arrangement of FIGS. 25A and 25B and delivering flow to a mass spectrometer.

FIGS. 25A and 25B illustrate an alternate embodiment of the invention wherein a 2-position, 10-port valve configuration allows switching between a quaternary HPLC flow path with low pressure mixing and a binary SFC flow path with low pressure mixing of modifiers and high pressure mixing of CO2 and modifier and where the system delivers terminal flow to a mass spectrometer (MS). FIG. 25A creates a flow path similar to the flow path of FIG. 16. However, rather than terminating in HPLC waste container 350, flow from the system terminates in mass spectrometer 640 which can typically accept flows of 0.05 to 2 mL/min of liquid flow. Secondary flow of FIG. 25A is illustrated as dashed lines. Valve 600 isolates the entire CO2 pumping system 370, 380 and 390, BPR 400 and SFC waste 410. Flow through the modifier inlet to mixer 340 is halted by plug 504. Metering pump 390 maintains communication with BPR 400 and SFC Waste 410 allowing it to remain safely charged. A schematic of the new quaternary HPLC/MS flow path is shown in FIG. 26A.

Figure 26B:
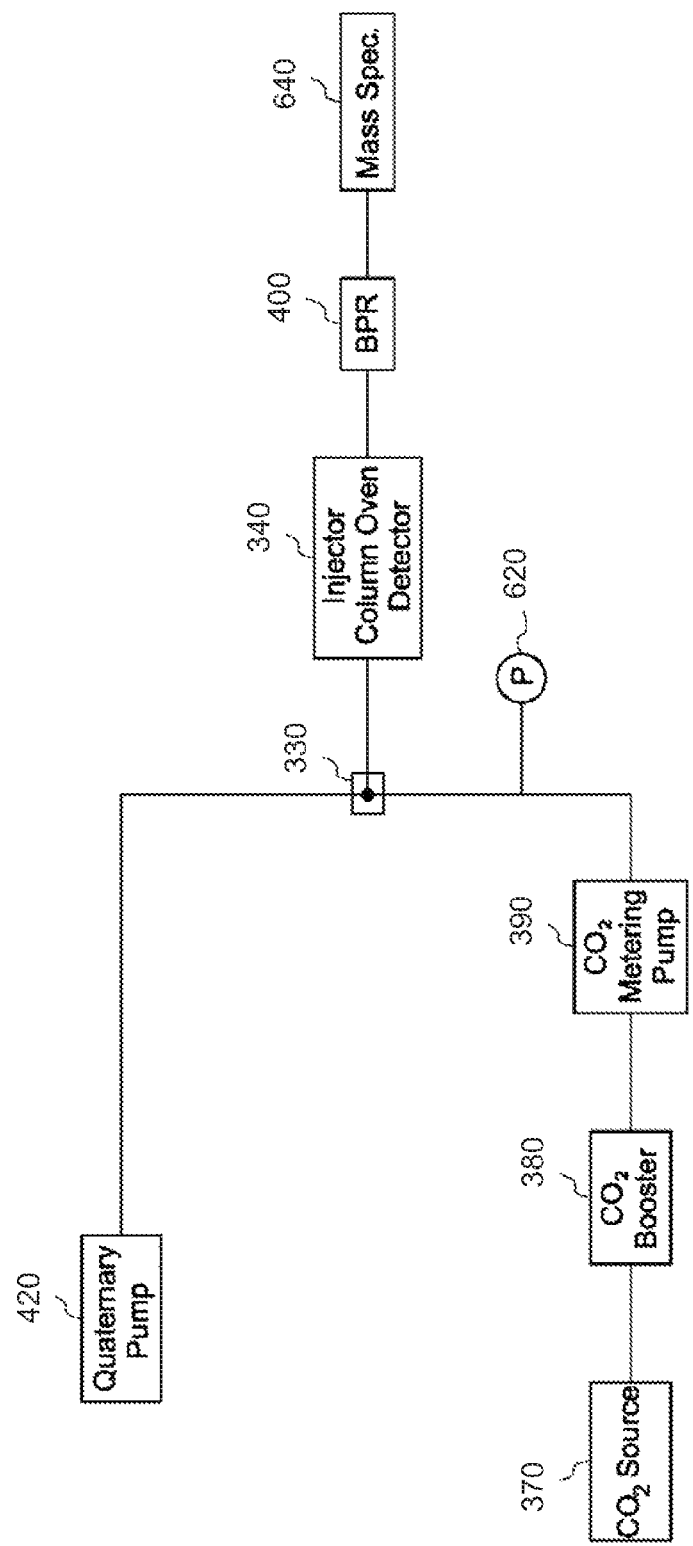

Switching valve 600 to its alternate position creates the valve configuration for the SFC/MS mode illustrated in FIG. 25B. In the primary path fluid exits pumps 390 and 420 and is combined in Mixer 330. Fluid is directed through instrument cluster 340 which may include a non-destructive detector such as UV and then flows to BPR 400. After BPR 400, CO2 expands as much as 500 fold and only the organic modifier must be evaporated by the mass spec. However, the evaporating CO2 does place a significant heating load in the MS inlet and auxiliary heating may be required to supplement heating system of mass spec 640. In the secondary path of FIG. 25B, the SFC Waste container 410 is isolated from the flow system. Hence waste container 410 has only the function of providing a vented relief to the secondary path of FIG. 25A. A schematic of the new SFC/MS flow path is shown in FIG. 26B.

All the various embodiments described are exemplary and do not constitute a full listing on possible implementations of the invention. Extensibility has been show in the use of eight and ten port valves, but 12-port or higher valves may also be considered. Rotary valves may be replaces with appropriate combinations of normally open and normally closed solenoids, but this is less preferred due to the complexity and loss of robustness. The principle components of the invention include 1) the ability to switch reversibly and in a single step all fluidic flow lines of an HPLC system to convert the flow system for SFC use and back, 2) reuse of at least one high pressure metering pumps in both flow modes of each configuration; 3) maintenance of fluidic communication between CO2 supply subsystem and the BPR in all modes of operation and 4) providing adequate ability to rinse common pathways with solvents miscible in both mobile phases for conversion between modes.

In general, it can readily be seen by one skilled in the art of pumping technology, that the invention described by this patent has truly broad applicability. Applications from uniform coating delivery to pharmaceutical dosing are include in the broad array of uses. In its essence, the patent reports a means of enhancing positive displacement pumps to deliver with high accuracy a significantly broader range of fluids currently believed too compressible for quantitative delivery without extraordinary means. Even in cases of current art, application of the embodiments of this patent can improve overall performance. The consideration that the invention can be implemented in the absence of detection or control by existing pump controllers extends its economic value.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. An apparatus, comprising:
a source of CO2 supply; and
a fluidic switch configured to be selectively switched between: a first switch position which provides a first flow path configuration through the switch for a liquid chromatographic (LC) system, and further provides a secondary flow path configuration; and a second switch position which provides a second flow path configuration through the switch for a supercritical fluid chromatographic system,
wherein the source of CO2 supply communicates with the secondary flow path configuration when the switch is in the first position, and with the second flow path configuration when the switch is in the second position.

2. The apparatus of claim 1, further comprising:
a backpressure regulation module,
wherein the switch provides the capability to maintain fluidic communication between said source of CO2 supply and said backpressure regulation module in both first and second said switch positions.

3. The apparatus of claim 1, wherein said source of CO2 supply comprises a CO2 metering pump.

4. The apparatus of claim 2, wherein said source of CO2 supply comprises a CO2 booster pump.

5. The apparatus of claim 1, further comprising:
an HPLC pump and a collection of HPLC modules for dual use within the supercritical fluid system and the liquid chromatographic system,
wherein said HPLC pump and HPLC modules remain in the first flow path configuration when the fluidic switch is in the first position and remain in the second flow path configuration when the fluidic switch is in the second position.

6. The apparatus of claim 5, wherein said HPLC pump is a high pressure positive displacement pump.

7. The apparatus of claim 6, wherein said high pressure positive displacement pump is one of a quaternary pump module, an isocratic pump module, or one unit of a binary pump module.

8. The apparatus of claim 5, wherein at least one pump in each of the first and second flow path configurations is capable of rinsing the flow path with a mobile phase compatible with both chromatographic systems.

9. The apparatus of claim 5, wherein the first and the second flow path configurations each terminate through a mass spectrometer.

10. A system, comprising:
a plurality of modules comprising a liquid chromatography (LC) system and a supercritical fluid chromatography (SFC) system; and
a fluidic switch,
wherein the plurality of modules include:
a back pressure regulator, and
a pump for compressible fluids,
wherein the switch is configured to be selectively switched between a first switch position and a second switch position to convert a flowpath between the LC system and the SFC system, and
wherein fluidic communication is maintained between the pump and the backpressure regulator module in both the first and second switch positions.

11. The system in claim 10, wherein the LC system modules are configured for dual use within the SFC system and the LC system and are included in the flow path for each of the SFC system and the LC system.

12. The system of claim 10, wherein at least one pump is configured to rinse the flow path with a mobile phase compatible with both the SFC system and the LC system.

13. The system of claim 10, wherein the modules further comprise:
a mass spectrometer, wherein each of the LC system and the SFC system is fluidically connected to said mass spectrometer.

14. The system of claim 10, wherein the LC system includes a high performance liquid chromatography system of modules.

15. The system of claim 10, wherein the LC system includes an ultra high performance liquid chromatography system of modules.

16. The system of claim 10, wherein the LC system includes modules capable of operating within system pressures up to 600 bar.

17. A process, comprising:
selectively switching a liquid chromatography (LC) pump, chromatographic system components, an upstream LC solvent source, a supercritical fluid chromatography (SFC) compressible fluid mobile phase source, and SFC system components including a back pressure regulator between a first flow path configuration for an LC mode of operation, and a second flow path configuration for an SFC mode of operation; and
maintaining fluidic communication between the SFC compressible fluid phase source and the back pressure regulator.

18. The process of claim 17, further comprising: rinsing a flowpath of the first flow path configuration and second flow path configuration to a state compatible with both modes of operation from either mode of operation.

19. The process of claim 17, further comprising: directing flow of each mode of operation to a mass spectrometer.

20. The process of claim 17, wherein the first flow path configuration includes a high performance liquid chromatography flow path or an ultra high performance liquid chromatography flow path.

* * * * *